United States Patent
Kikitsu et al.

(10) Patent No.: US 10,837,953 B2
(45) Date of Patent: Nov. 17, 2020

(54) SENSOR

(71) Applicant: Kabushiki Kaisha Toshiba, Tokyo (JP)

(72) Inventors: Akira Kikitsu, Kanagawa (JP); Hitoshi Iwasaki, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 686 days.

(21) Appl. No.: 15/438,793

(22) Filed: Feb. 22, 2017

(65) Prior Publication Data

US 2017/0363606 A1 Dec. 21, 2017

(30) Foreign Application Priority Data

Jun. 16, 2016 (JP) ................................. 2016-119700

(51) Int. Cl.
*G01N 33/483* (2006.01)
*H01L 43/08* (2006.01)
(Continued)

(52) U.S. Cl.
CPC ..... *G01N 33/4833* (2013.01); *G01N 21/6428* (2013.01); *G01N 33/5005* (2013.01);
(Continued)

(58) Field of Classification Search
CPC ........... G01N 33/4833; G01N 21/6428; G01N 33/5005; G01N 2021/7786;
(Continued)

(56) References Cited

U.S. PATENT DOCUMENTS 5,563,067 A 10/1996 Sugihara et al.
6,297,025 B1 10/2001 Sugihara et al.
(Continued)

FOREIGN PATENT DOCUMENTS

JP 2000-055874 2/2000
JP 2004-028723 1/2004
(Continued)

OTHER PUBLICATIONS

Hierlemann et al., "Growing Cells Atop Microelectronic Chips: Interfacing Electrogenic Cells In Vitro With CMOS-Based Microelectrode Arrays," *Proceedings of the IEEE*, vol. 9, No. 22, pp. 252-284, Feb. 2011.
(Continued)

*Primary Examiner* — William H. Beisner
*Assistant Examiner* — Danielle B Henkel
(74) *Attorney, Agent, or Firm* — Finnegan, Henderson, Farabow, Garrett & Dunner, L.L.P.

(57) ABSTRACT

According to one embodiment, a sensor includes a nonmagnetic layer and a plurality of magnetic field sensors. The nonmagnetic layer has a first surface and a second surface. The magnetic field sensors are arranged along the second surface. The second surface is between the first surface and the magnetic field sensors. Each of the magnetic field sensors includes a first magnetic layer, a second magnetic layer provided between the first magnetic layer and the nonmagnetic layer, and an intermediate layer provided between the first magnetic layer and the second magnetic layer. The intermediate layer is nonmagnetic. A distance between the first surface and the second magnetic layer is not more than a pitch of the magnetic field sensors.

18 Claims, 21 Drawing Sheets

(51) Int. Cl.

| | |
|---|---|
| *H01L 43/10* | (2006.01) |
| *H01L 43/12* | (2006.01) |
| *G01N 21/64* | (2006.01) |
| *G01N 33/50* | (2006.01) |
| *G01R 15/20* | (2006.01) |
| *G01R 33/09* | (2006.01) |
| *G01N 21/77* | (2006.01) |
| *H01L 43/02* | (2006.01) |

(52) U.S. Cl.
CPC ......... *G01R 15/205* (2013.01); *G01R 33/093* (2013.01); *G01R 33/098* (2013.01); *H01L 43/08* (2013.01); *H01L 43/10* (2013.01); *H01L 43/12* (2013.01); *G01N 2021/7786* (2013.01); *G01N 2201/068* (2013.01); *H01L 43/02* (2013.01)

(58) Field of Classification Search
CPC ............ G01N 2201/068; G01R 15/205; G01R 33/093; G01R 33/098; H01L 43/08; H01L 43/10; H01L 43/12; H01L 43/02
See application file for complete search history.

(56) References Cited

U.S. PATENT DOCUMENTS

| | | | |
|---|---|---|---|
| 6,890,762 B1 | 5/2005 | Sugihara et al. | |
| 2004/0000918 A1 | 1/2004 | Sanoner et al. | |
| 2004/0120185 A1 | 6/2004 | Kang et al. | |
| 2005/0087000 A1* | 4/2005 | Coehoorn | B82Y 25/00 73/53.01 |
| 2005/0100930 A1 | 5/2005 | Wang et al. | |
| 2005/0138886 A1 | 6/2005 | Sanoner et al. | |
| 2007/0210785 A1 | 9/2007 | Sanoner et al. | |
| 2010/0109657 A1 | 5/2010 | Voegeli | |
| 2010/0194386 A1 | 8/2010 | Prins et al. | |
| 2011/0163744 A1 | 7/2011 | Nakayama et al. | |
| 2011/0279901 A1 | 11/2011 | Watanabe | |
| 2012/0064567 A1 | 3/2012 | Stakenborg et al. | |
| 2013/0230913 A1 | 9/2013 | Florescu | |
| 2013/0330828 A1 | 12/2013 | Hayden et al. | |

FOREIGN PATENT DOCUMENTS

| | | |
|---|---|---|
| JP | 2007-248994 | 9/2007 |
| JP | WO 2009/130814 A | 10/2009 |
| JP | 2012-013579 | 1/2012 |
| JP | 2012-507735 A | 3/2012 |
| JP | 2013-543593 A | 12/2013 |
| JP | 2014-509397 A | 4/2014 |
| JP | 2015-210233 | 11/2015 |
| WO | WO 2012/048288 A1 | 4/2012 |
| WO | WO 2016/104517 A1 | 6/2016 |

OTHER PUBLICATIONS

Hizawa et al., "Characteristics of Highly Sensitive pH Sensors with Charge Accumulation Operation," *Japanese Journal of Applied Physics*, vol. 45, No. 12, pp. 9259-9263, 2006.

Tanenaga et al., "Label-Free Acetylcholine Image Sensor Based on Charge Transfer Technology for Biological Phenomenon Tracking," *Japanese Journal of Applied Physics*, vol. 51, pp. 027001-1-027001-5, 2012.

Singh et al., "A CMOS/Thin-Film Fluorescence Contact Imaging Microsystem for FNA Analysis," *IEEE Transactions on Circuits and Systems-I*, vol. 57, No. 5, May 2010, pp. 1029-1038.

Tanenaga et al. "Charge Accumulation Type Hydrogen Ion Image Sensor with High PH Resolution," *Japanese Journal of Applied Phusics*, vol. 50, 2011, pp. 027001-1-027001-5.

Johnson et al., "A 768-channel CMOS Microelectrode Array With Angle Sensitive Pixels for Neuronal Recording," *IEEE Sensors Jorunal*, vol. 13, No. 9, Sep. 2013, pp. 3211-3218.

* cited by examiner

SENSOR

CROSS-REFERENCE TO RELATED APPLICATIONS

This application is based upon and claims the benefit of priority from Japanese Patent Application No. 2016-119700, filed on Jun. 16, 2016; the entire contents of which are incorporated herein by reference.

FIELD

Embodiments described herein relate generally to a sensor.

BACKGROUND

A sensor is being developed to perform biomeasurement by disposing a specimen such as cells, etc., on a semiconductor chip. In such a sensor, it is desirable to sense the state of the specimen accurately while suppressing damage to the specimen.

DETAILED DESCRIPTION

Figure 1A:
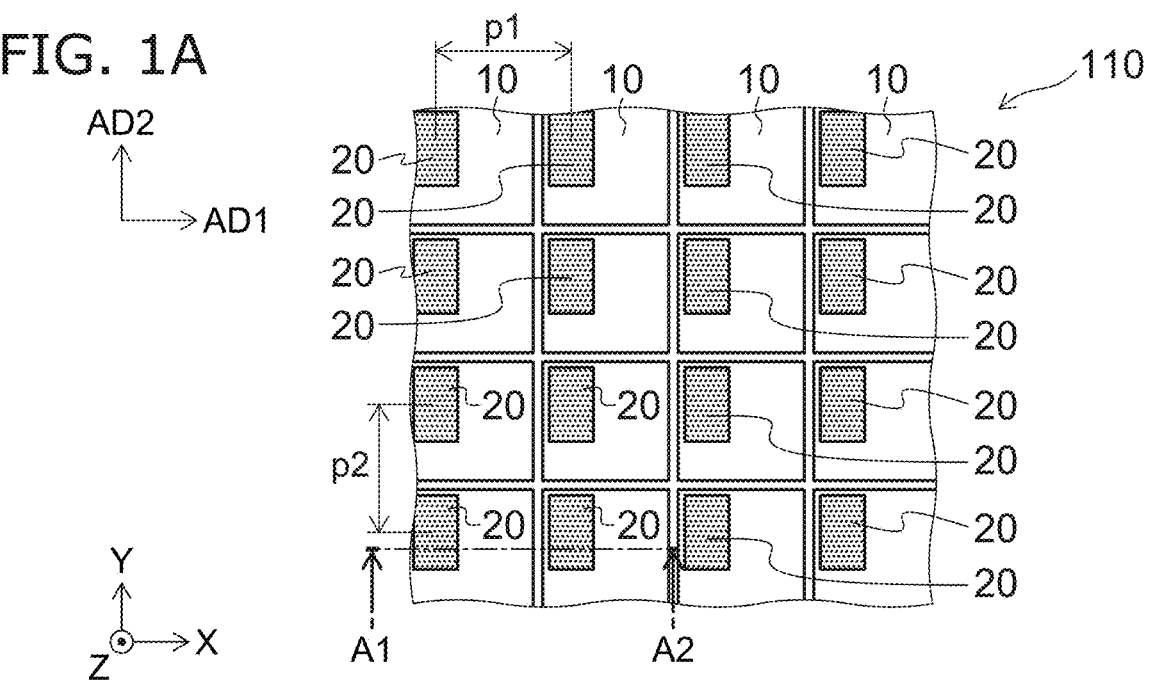
FIG. 1A to FIG. 1D are schematic views illustrating a sensor according to a first embodiment.

According to one embodiment, a sensor includes a nonmagnetic layer and a plurality of magnetic field sensors. The nonmagnetic layer has a first surface and a second surface. The magnetic field sensors are arranged along the second surface. The second surface is between the first surface and the magnetic field sensors. Each of the magnetic field sensors includes a first magnetic layer, a second magnetic layer provided between the first magnetic layer and the nonmagnetic layer, and an intermediate layer provided between the first magnetic layer and the second magnetic layer. The intermediate layer is nonmagnetic. A distance between the first surface and the second magnetic layer is not more than a pitch of the magnetic field sensors.

Various embodiments will be described hereinafter with reference to the accompanying drawings.

The drawings are schematic and conceptual; and the relationships between the thickness and width of portions, the proportions of sizes among portions, etc., are not necessarily the same as the actual values thereof. Further, the dimensions and proportions may be illustrated differently among drawings, even for identical portions.

In the specification and drawings, components similar to those described or illustrated in a drawing thereinabove are marked with like reference numerals, and a detailed description is omitted as appropriate.

First Embodiment

FIG. 1A to FIG. 1D are schematic views illustrating a sensor according to a first embodiment.

Figure 1B:
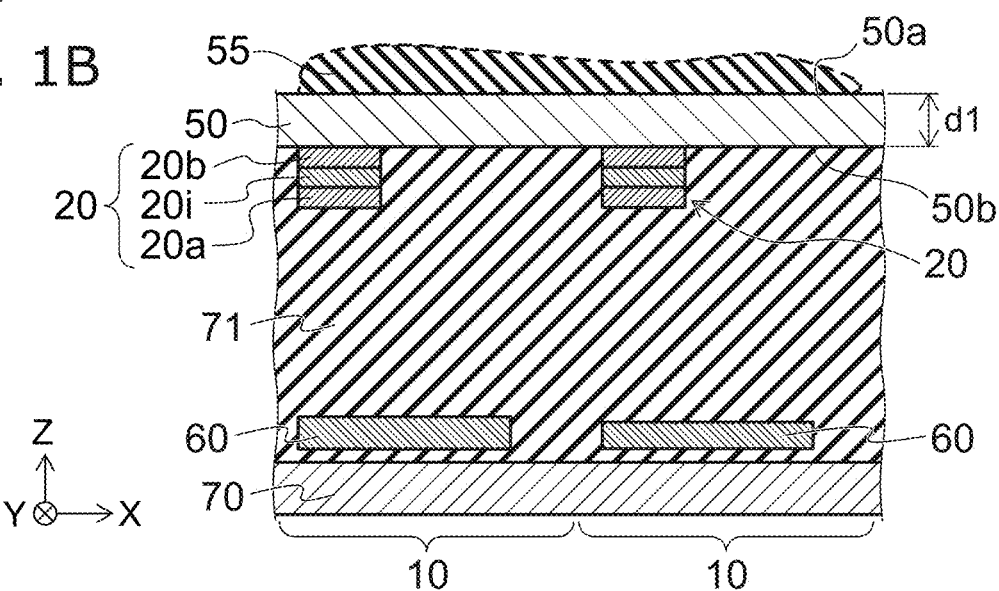
Figures 1C, 1D:
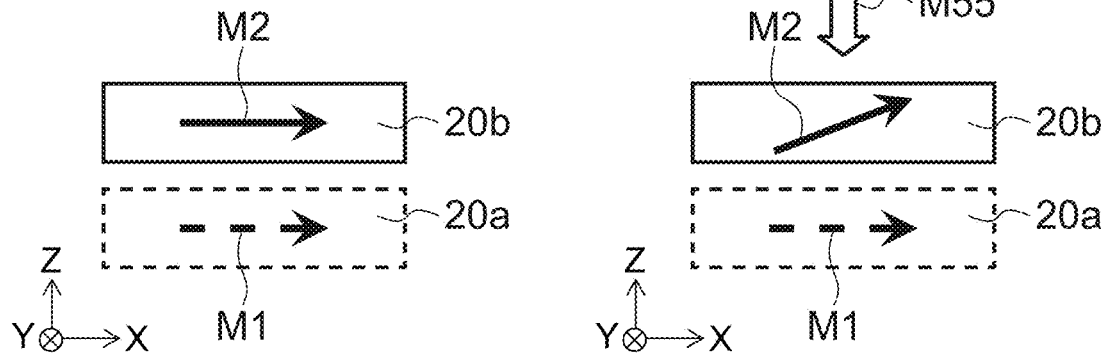

FIG. 1A is a plan view. FIG. 1B is a cross-sectional view of FIG. 1A along the line A1-A2 in FIG. 1. FIG. 1C illustrates a state of the magnetization in magnetic layers. FIG. 1D illustrates another state of the magnetization in the magnetic layers.

As shown in FIG. 1B, the sensor 110 according to the embodiment includes a nonmagnetic layer 50 and multiple magnetic field sensors 20. The nonmagnetic layer 50 has a first surface 50a and a second surface 50b. The second surface 50b is the surface opposite to the first surface 50a. The multiple magnetic field sensors 20 are arranged along the second surface 50b.

A direction from the second surface 50b toward the first surface 50a is taken as a Z-axis direction. One direction perpendicular to the Z-axis direction is taken as an X-axis direction. A direction perpendicular to the Z-axis direction and the X-axis direction is taken as a Y-axis direction.

For example, the second surface 50b spreads along the X-Y plane. The second surface 50b may be a curved surface.

The second surface 50b is between the first surface 50a and the multiple magnetic field sensors 20. In other words, the second surface 50b is the surface for the side of the multiple magnetic field sensors 20.

In the example as shown in FIG. 1A, the multiple magnetic field sensors 20 are arranged in the X-axis direction and the Y-axis direction. For example, the multiple magnetic field sensors 20 are arranged in a matrix configuration.

Multiple sensing components 10 are provided in the sensor 110. One of the multiple sensing components 10 includes at least one of the multiple magnetic field sensors 20. For example, the multiple sensing components 10 are arranged in the X-axis direction and the Y-axis direction. For example, the multiple sensing components 10 are arranged in a matrix configuration.

For example, at least a portion of the multiple magnetic field sensors 20 is arranged along a first arrangement direction AD1. The first arrangement direction AD1 is aligned with the second surface 50b. The first arrangement direction AD1 is, for example, the X-axis direction. The arrangement pitch of the multiple magnetic field sensors 20 in the first arrangement direction AD1 is, for example, a first pitch p1.

At least a portion of the multiple magnetic field sensors 20 is arranged along a second arrangement direction AD2. The second arrangement direction AD2 crosses the first arrangement direction AD1 and is aligned with the second surface 50b. The second arrangement direction AD2 is, for example, the Y-axis direction. The arrangement pitch of the multiple magnetic field sensors 20 in the second arrangement direction AD2 is, for example, a second pitch p2. The second arrangement direction AD2 may be tilted with respect to the first arrangement direction AD1.

For example, at least a portion of the multiple sensing components 10 is arranged along the first arrangement direction AD1. The arrangement pitch of the multiple sensing components 10 in the first arrangement direction AD1 is, for example, the first pitch p1. At least a portion of the multiple sensing components 10 is arranged along the second arrangement direction AD2. The arrangement pitch of the multiple sensing components 10 in the second arrangement direction AD2 is, for example, the second pitch p2.

As shown in FIG. 1B, a specimen 55 can be placed at the first surface 50a. The nonmagnetic layer 50 is, for example, a specimen placement layer. For example, the specimen 55 contacts the first surface 50a. The first surface 50a is, for example, a specimen placement surface.

The specimen 55 is, for example, cells, etc. The specimen 55 includes, for example, nerves. Examples of the specimen 55 are described later.

Each (at least one) of the multiple magnetic field sensors 20 includes a first magnetic layer 20a, a second magnetic layer 20b, and an intermediate layer 20i. The second magnetic layer 20b is provided between the first magnetic layer 20a and the nonmagnetic layer 50. The intermediate layer 20i is provided between the first magnetic layer 20a and the second magnetic layer 20b. The intermediate layer 20i is nonmagnetic.

As shown in FIG. 1B, a base body 70 (e.g., a substrate), an insulating layer 71, and a sensor circuit portion 60 are provided in the example. The insulating layer 71 and the sensor circuit portion 60 are provided between the base body 70 and the nonmagnetic layer 50. A portion of the insulating layer 71 is provided between the base body 70 and the multiple magnetic field sensors 20. Another portion of the insulating layer 71 is provided between the base body 70 and the sensor circuit portion 60. Another portion of the insulating layer 71 is provided between the nonmagnetic layer 50 and the sensor circuit portion 60.

The sensor circuit portion 60 is connected to at least one of the multiple magnetic field sensors 20. For example, the sensor circuit portion 60 and at least one of the multiple magnetic field sensors 20 are electrically connected by a conductive body (an interconnect, etc., described below) that is not illustrated in FIG. 1B.

In the example, at least a portion of the multiple magnetic field sensors 20 is disposed between the nonmagnetic layer 50 and at least a portion of the sensor circuit portion 60 in the Z-axis direction (the direction from the second surface 50b toward the first surface 50a). For example, the sensor circuit portion 60 and the multiple magnetic field sensors 20 are stacked. Thereby, the surface area of the sensor can be reduced.

The specimen 55 is placed on the first surface 50a; and a pulse signal is generated in the specimen 55. A magnetic field that corresponds to the pulse signal is applied to at least one of the multiple magnetic field sensors 20. A magnetic field that corresponds to the pulse signal of the specimen 55 is sensed by the at least one of the multiple magnetic field sensors 20.

For example, in FIG. 1C, the strength of the pulse signal is low. At this time, the strength of the magnetic field also is low. In this state, for example, a first magnetization M1 of the first magnetic layer 20a is aligned with one direction; and a second magnetization M2 of the second magnetic layer 20b also is aligned with the one direction. In the example, the second magnetization M2 is parallel to the first magnetization M1.

On the other hand, in FIG. 1D, the strength of the pulse signal is high. At this time, the strength of a magnetic field M55 generated in the specimen 55 also is high. In this state, for example, the direction of the second magnetization M2 of the second magnetic layer 20b changes its direction from that of the direction illustrated in FIG. 1C. On the other hand, the direction of the first magnetization M1 of the first magnetic layer 20a substantially does not change. Then, the angle between the first magnetization M1 and the second magnetization M2 changes from the angle illustrated in FIG. 1C. The electrical resistance of the magnetic field sensor 20 including the first magnetic layer 20a and the second magnetic layer 20b changes corresponding to the change of the angle. Thus, the magnetic field sensor 20 detects the magnetic field that corresponds to the pulse signal generated in the specimen 55. At least one of the multiple magnetic field sensors 20 outputs a signal corresponding to the pulse signal generated in the specimen 55.

For example, the change of the electrical resistance corresponding to the change of the magnetic field is based on the GMR (giant magnetoresistance) effect or the TMR (tunneling magnetoresistance) effect. In the example shown in FIG. 1C, the second magnetization M2 is parallel to the first magnetization M1. In the embodiment, the angle (the direction) between these magnetizations is arbitrary. In the example recited above, the direction of the first magnetization M1 substantially does not change. For example, the first magnetic layer 20a is a reference layer; and the second magnetic layer 20b is a free layer. In the embodiment, both the first magnetization M1 and the second magnetization M2 may change.

The magnetic field at the second magnetic layer 20b is reduced with the distance from the specimen 55 to the second magnetic layer 20b. When the distance is not more than a threshold value, the magnetic field sensor can detect the pulse signal generated in the specimen 55 appropriately.

As shown in FIG. 1B, a distance d1 is the distance between the first surface 50a and the second magnetic layer 20b. When the specimen 55 is placed on the first surface 50a, the distance d1 corresponds to the distance between the specimen 55 and the second magnetic layer 20b.

In the embodiment, the distance d1 (the distance between the first surface 50a and the second magnetic layer 20b) is not more than the pitch (the arrangement pitch) of the multiple magnetic field sensors 20. The pitch may be the shorter one of the first pitch p1 and the second pitch p2. For example, the pitch is about 10 μm; and in such a case, the distance d1 is 10 micrometers (inn) or less. Thereby, as described below, the activity of the specimen can be sensed more accurately through the magnetic field.

The relationship between the distance d1 and the sensed signal will now be described.

FIG. 2A to FIG. 2D are schematic views illustrating characteristics of the sensed signals from the specimen.

Figure 2A:
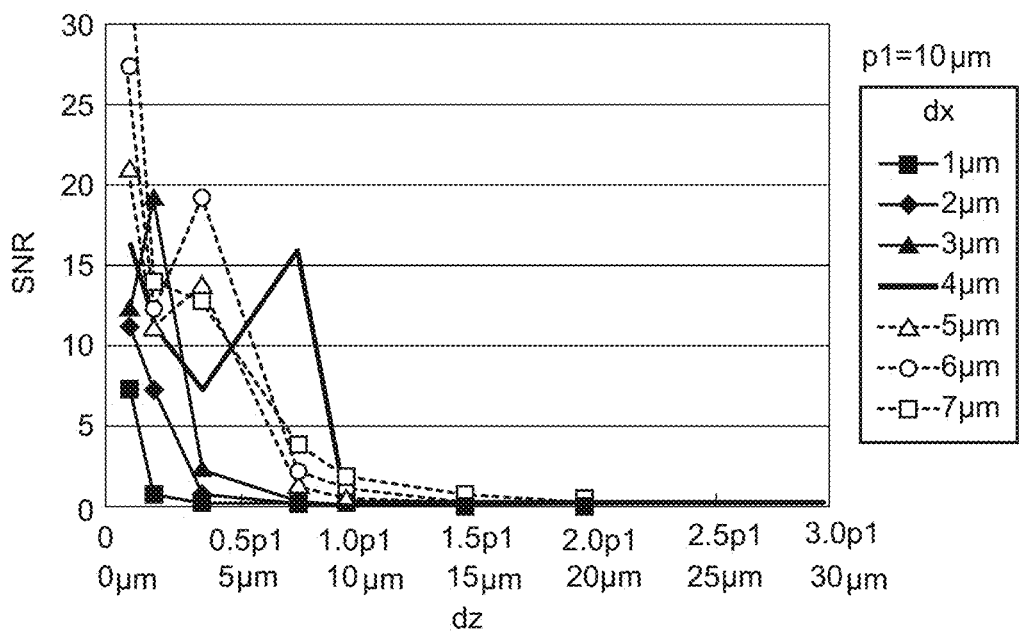
FIG. 2A to FIG. 2D are schematic views illustrating characteristics of the sensor and the specimen.
Figure 2B:
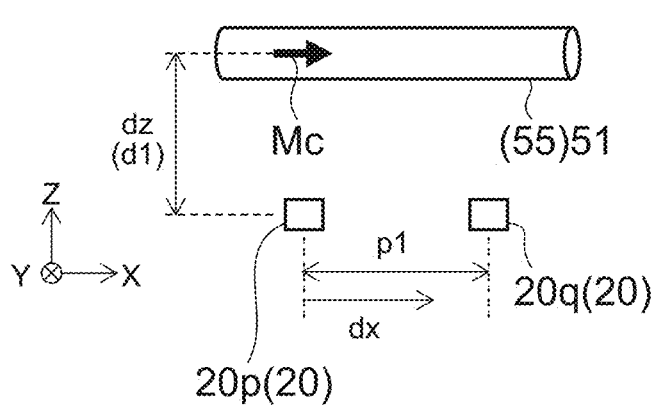
Figure 2C:
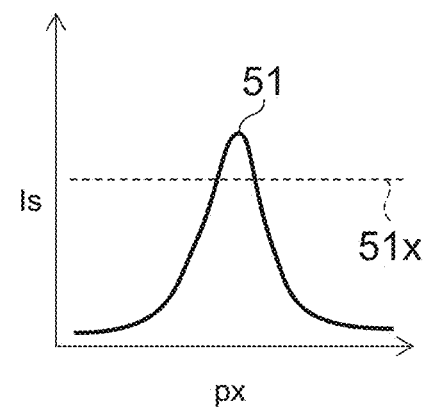
Figure 2D:
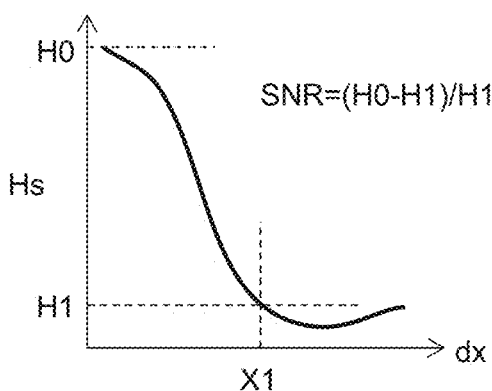

FIG. 2A is a graph illustrating simulation results of the sensed signal. FIG. 2B is a schematic view showing the model used in the simulation. FIG. 2C is a schematic view illustrating the characteristics of the localized electric current in the specimen 55. FIG. 2D is a schematic view illustrating the magnetic field sensed by the sensor. In the simulation, a living body is used as the specimen 55. The living body is, for example, a neuron.

As shown in FIG. 2B, a neuron 51 (the specimen 55) extends in the X-axis direction in the model of the simulation. A current moment Mc is generated and transported in the neuron 51. For example, the current moment Mc is caused by a flow of ions or the like into or out from the neuron 51 through many ion channels on the neuron. For example, an electric potential distribution generated by the ion flow (action potential) moves through the neuron 51. The movement of the electric potential distribution corresponds to the movement of a localized electric charge (action current). The movement of the localized electric charge corresponds to a localized electric current (an equivalent pulse electric current).

The horizontal axis of FIG. 2C is a position px along the X-axis direction. The vertical axis is a current Is. As illustrated in FIG. 2C, in the neuron 51 the intensity of the current Is changes with the position px at some specific time. The current Is has a peak (a maximum) at a position along the X-axis direction, and the current Is decreases with the distance px. On the other hand, for the case where the specimen 55 is an electric conductor 51x, the intensity of the current Is that flows through the conductor 51x is constant over the position px at some specific time even if a pulse current flows. Thus, in the case where the specimen 55 is a living body such as the neuron 51, a spatially localized current Is flows.

In the simulation, a specialized model where such a spatially localized electric current Is is employed. As shown in FIG. 2B, two magnetic field sensors 20 (magnetic field sensors 20p and 20q) are provided. A distance dz is the distance (the distance along the Z-axis direction) between the neuron 51 and these magnetic field sensors 20. The distance dz corresponds to the distance d1 in FIG. 1B. The distance between the centers of the two magnetic field sensors 20p and 20q corresponds to the first pitch p1. An offset dx is the distance along the X-axis direction from the center of the magnetic field sensor 20p.

For example, at a moment, intensity of the magnetic field that is generated from the electric current moment Mc is large at the magnetic field sensor 20p and is small at the magnetic field sensor 20q. Thereby, for example, the spatial distribution of the electric current moment Mc is sensed. A temporal change in the detected signal means the temporal change in the spatial distribution of the electric current moment Mc. In other words, the temporal change in the activities in the neuron 51 can be detected. The magnetic field detected at the magnetic field sensors 20, that are different in their positions, is evaluated by the simulation.

FIG. 2D illustrates the magnetic field generated by the electric current moment Mc. The horizontal axis of FIG. 2D is the offset dx. The vertical axis is a strength Hs of the magnetic field. As shown in FIG. 2D, Hs is low when the offset dx is large. For example, Hs at dx=0 is a strength H0, and Hs at dx=x1 is a strength H1. Here, a parameter SNR is defined as follows.

$$SNR=(H0-H1)/H1$$

The parameter SNR corresponds to the difference in the magnetic fields sensed by two magnetic field sensors 20, where their positions are different. High SNR means that the spatial resolution of the magnetic field sensing is high.

The Sarvas equation (Jukka Sarvas: Phys. Med. Biol., 1987, Vol. 32, No. 1, pp. 11-12) is used in the simulation. In the simulation, the electric current moment Mc is set as $20 \times 10^{-6}$ nAm. The distance dz (the distance along the Z-axis direction between the magnetic field sensor 20 and the neuron 51) is changed in the range of not less than 1 μm and not more than 40 μm.

FIG. 2A illustrates the simulation results. The horizontal axis is the distance dz. In the example, the pitch of the two magnetic field sensors 20 is the first pitch p1; and the first pitch p1 is 10 μm. The distance dz is also expressed using the first pitch p1 on the horizontal axis. When dz is 10 μm, is corresponds to the first pitch p1. The vertical axis is the parameter SNR. In FIG. 2A, the offset dx is varied from 1 μm to 7 μm.

In FIG. 2A, it is clear that the parameter SNR becomes extremely low when the distance dz exceeds 15 μm. When the distance dz is 15 μm or less, the parameter SNR is high. In particular, the parameter SNR becomes extremely high when the distance dz is 10 μm or less. In other words, extremely high SMR is obtained when the distance dz is not more than the pitch (the first pitch p1). These tendencies are unique and critical.

In a reference example of the case where the specimen 55 is a conductor 51x as described in FIG. 2C, the current Is that flows through the conductor 51x is constant over the position px. Therefore, the strength Hs of the magnetic field also is constant over the offset dx (the distance). In other words, in the reference example, the strength Hs of the magnetic field is constant and is independent of the offset dx in the graph of FIG. 2D. Accordingly, in the reference example, the parameter SNR is independent of the distance dz and is always 0.

In the case where the specimen 55 is a living body such as the neuron 51, the current Is has a spatial distribution as shown in FIG. 2C. Magnetic field generated by such a current Is is no longer constant over the offset dx (referring to FIG. 2D). This situation results in the unique characteristics of SNR shown in FIG. 2A. The unique characteristics illustrated in FIG. 2A do not occur in the case where the specimen 55 is the conductor 51x. This unique characteristics illustrated in FIG. 2A were discovered for the first time by the inventor of the application. In the embodiment, the sensor is, for example, a living body sensor.

Characteristics similar to those illustrated in FIG. 2A are obtained when the pitch (the first pitch p1) is set to more or less than 10 μm. In other words, a high SNR is obtained when the distance dz is not more than the first pitch p1. In the embodiment, the distance d1 (the distance between the first surface 50a and the second magnetic layer 20b) is not more than the first pitch p1. For example, when the first pitch p1 is 10 μm, the distance d1 is set to 10 μm or less. Thereby, a high SNR is obtained. For example, a high spatial resolution is obtained. For example, a high time resolution is obtained.

According to the embodiment, a sensor system, which can detect the activity in the specimen more accurately, is provided.

In the embodiment, at least one of the multiple magnetic field sensors 20 outputs a signal corresponding to the pulse signal (e.g., the equivalent pulse current) in the specimen 55. Thereby, the activity of the specimen 55 is sensed.

In the embodiment, it is favorable for the distance d1 to be 1 nanometer (nm) or more. By setting the distance d1 to be 1 nm or more, for example, the sensor is easy to manufacture, and is stable in the sensing capability.

For example, the position where dx=7 μm in FIG. 2A corresponds to a middle point between two magnetic field sensors 20 with the first pitch p1 of 14 μm. For example, when four magnetic field sensors 20 are arranged in a square lattice in the X-Y plane with p1=10 μm and p2=10 μm, the middle position on the diagonal line corresponds to the point of dx=7 μm in FIG. 2A.

For example, when the pitch of the multiple magnetic field sensors 20 is 14 μm or less, a high spatial resolution and/or a high temporal resolution is obtained by setting the distance dz to 10 μm or less.

In the embodiment, the pitch may be 14 μm or more. For that case, when the number of the multiple magnetic field sensors 20 is large (e.g., four or more), the current moment Mc can be estimated by using magnetic field detected by the sensors 20 other than the nearest two sensors.

In the embodiment, the first pitch p1 (referring to FIG. 1A) is, for example, not less than 2 times and not more than 1000 times the distance d1. The second pitch p2 (referring to FIG. 1A) is, for example, not less than 2 times and not more than 1000 times the distance d1. Thereby, for example, a high spatial resolution is obtained. For example, a high temporal resolution is obtained.

At least one of the first pitch p1 or the second pitch p2 is, for example, not less than 300 nm and not more than 20 μm.

In the example recited above, the electric current pulse flowing through the neuron 51 is sensed. For example, the embodiment also can sense different activities in the specimen 55 other than the neuron 51.

The first reference example uses a SQUID for sensing the activity in the cell. In such a case, the spatial resolution is insufficient because the sensing coil has a size of about 1 mm to 10 mm. In the second reference example, a GMR element is scanned over a specimen. In such a case, it is difficult to sense the temporal change of the activity in the specimen with high sensing rate. In the third reference example, the discharge/absorption of a designated protein that accompanies the activity in the nerve is sensed by using the change of fluorescence. The fourth reference example senses the discharge/absorption of designated ions that accompany the activity by using an ion sensor. In the third and fourth reference examples, the sensing is indirect because substances discharged as a result of the activity are sensed. Furthermore, high-speed sensing is difficult. The fifth reference example detects the activity in the specimen (the pulse current flowing through the nerve) by touching electrodes to the specimen. In such a case, the sensing process has large influence on the activity in the specimen. In other words, it is relatively invasive sensing.

Conversely, in the embodiment, the condition of the specimen 55 is sensed by measuring the magnetic field generated from the specimen 55. Therefore, the sensing process has little influence on the activity in the specimen. Furthermore, a change in the activities in the specimen 55 can be sensed at a high sensing rate.

An example of the specimen 55 will now be described.

Figure 3:
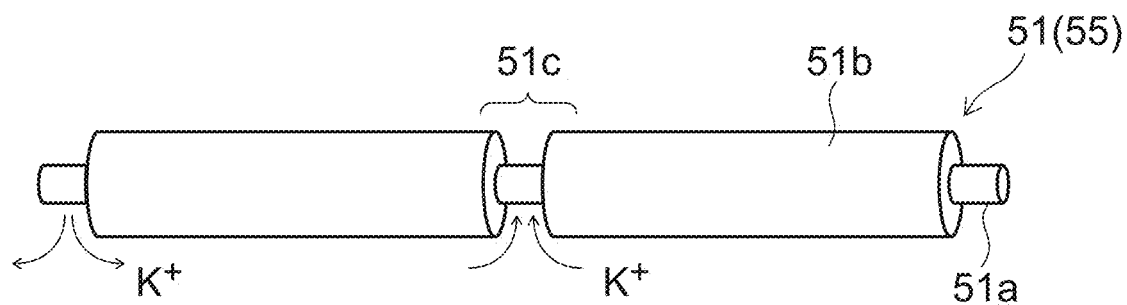
FIG. 3 is a schematic view illustrating a portion of a specimen to be sensed by the sensor according to the embodiment.

FIG. 3 is a schematic view illustrating a specimen to be sensed in the sensor according to the embodiment.

As shown in FIG. 3, the neuron 51 is one example of the specimen 55. In the neuron 51, multiple myelin sheaths 51b cover a nerve fiber 51a. A portion of the nerve fiber 51a is not covered with the myelin sheaths 51b, and the portion is called as a node of Ranvier 51c. For example, an equivalent electric current pulse flows through the nerve fiber 51a. The nerve fiber 51a is insulative. When information is transmitted through the nerve, a flow (inflow or outflow) of ions 51d (e.g., Na ions, K ions, etc.) is generated by the opening and closing of an ion channel at the node of Ranvier 51c. The timing of the flow of the ions 51d is different between the nodes of Ranvier 51c. Thereby, a difference (a distribution) of the electric potential occurs along the multiple nodes of Ranvier 51c. The difference of the electric potentials moves with time along the nerve fiber. Thereby, the information is transmitted.

The movement of the electric potential distribution through the nerve fiber 51a is equivalent to a movement of electric charge, that is, an electric current. Then, a magnetic field is generated by the equivalent electric pulse current corresponding to the movement of the electric potential distribution. The electric current Is that corresponds to the movement of the electric potential distribution changes along the nerve fiber 51a, as described in FIG. 2C. In other words, a spatial distribution of the current Is occurs.

Therefore, to investigate the specimen 55 including the neuron 51, the Biot-Savart law, which is generally used for a magnetic field generated by an electric current, cannot be applied. Therefore, the Sarvas formula is used for the simulation recited in this embodiment.

Figure 4:
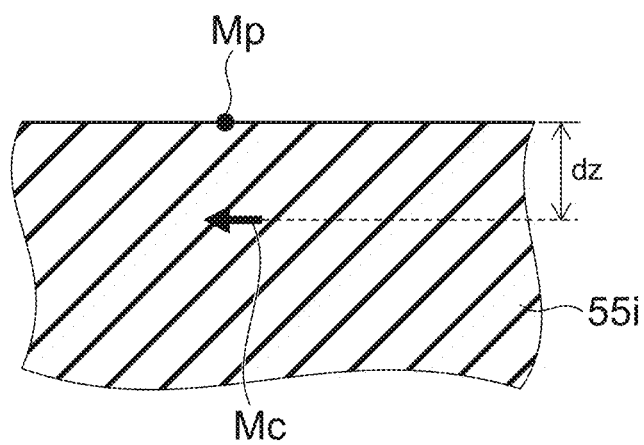
FIG. 4 is a schematic view illustrating a model for the simulation.

FIG. 4 is a schematic view illustrating the model of the simulation.

As shown in FIG. 4, the current moment Mc moves through an insulating medium 55i. The magnetic field at a measurement point Mp is estimated by the Sarvas formula. One example of the simulation results is shown in FIG. 2A. Another example of the simulation results will now be described.

Figure 5A:
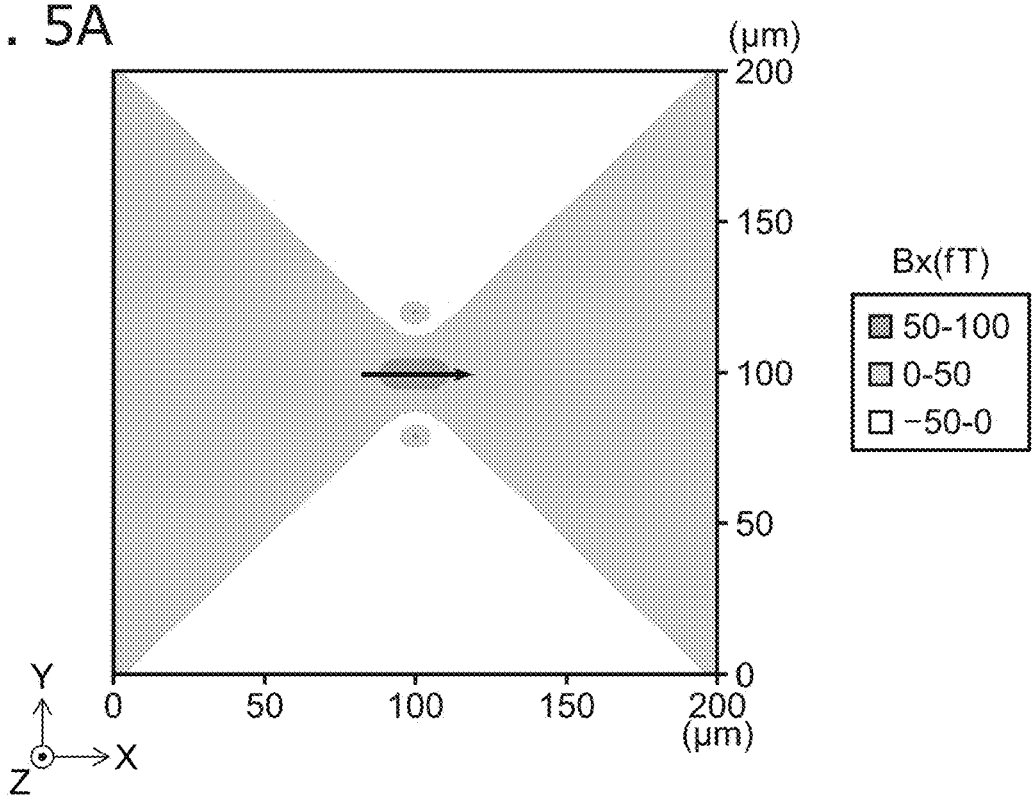
FIG. 5A and FIG. 5B are schematic views illustrating the simulation results.
Figure 5B:
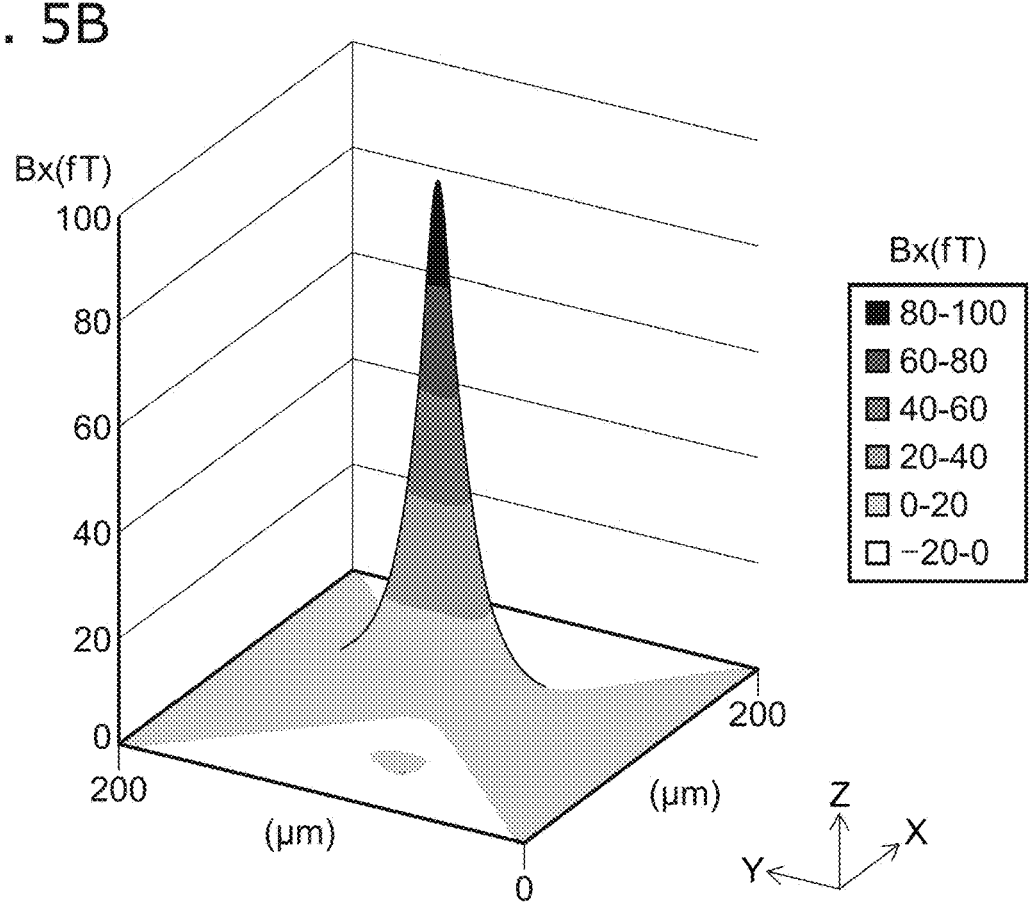

FIG. 5A and FIG. 5B are schematic views illustrating the simulation results.

These figures illustrate the spatial distribution of a magnetic field Bx in the X-axis direction when the distance d1 is 10 μm. The calculated region is a square of a side 200 μm. The spatial resolution of the calculation is 1 μm. The orientation of the current moment Mc is shown by an arrow. As shown in FIG. 5A and FIG. 5B, the peak of the strength of the magnetic field Bx is about 100 fT. The planar distribution of the strength of the magnetic field Bx decreases abruptly for a distance (a distance in the X-Y plane) beyond about 10 μm.

Figure 6A:
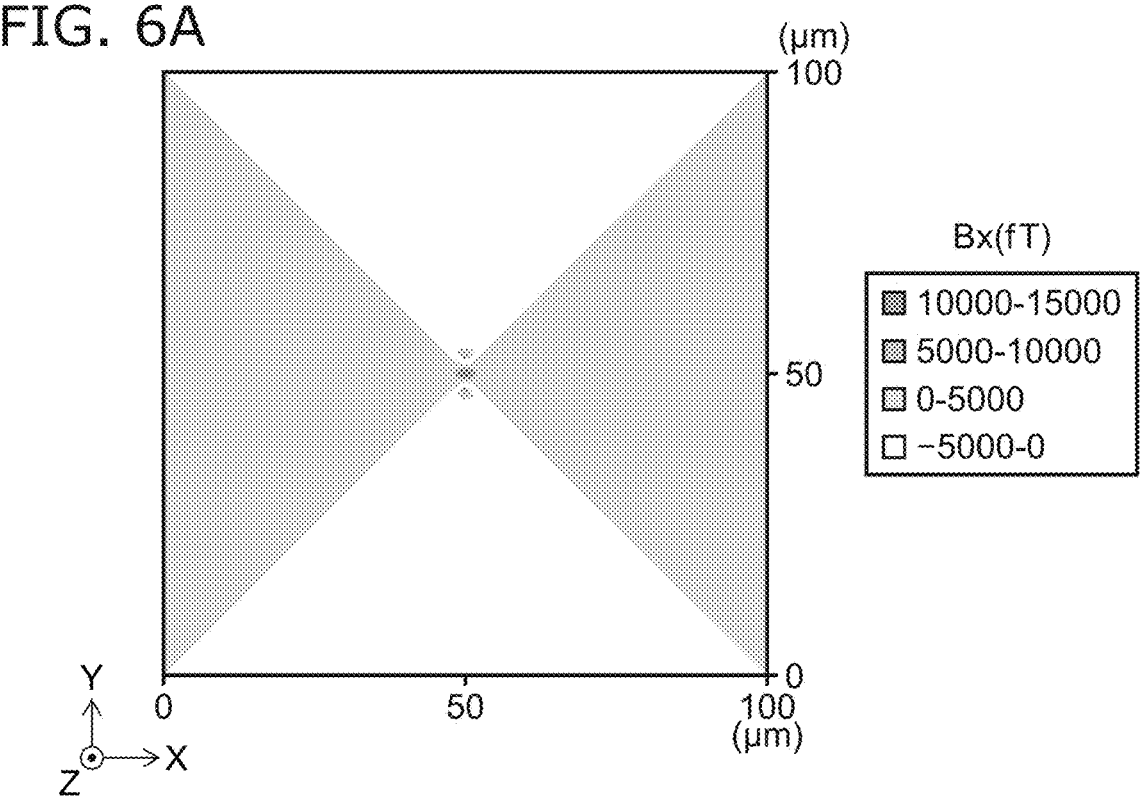
FIG. 6A and FIG. 6B are schematic views illustrating the simulation results.
Figure 6B:
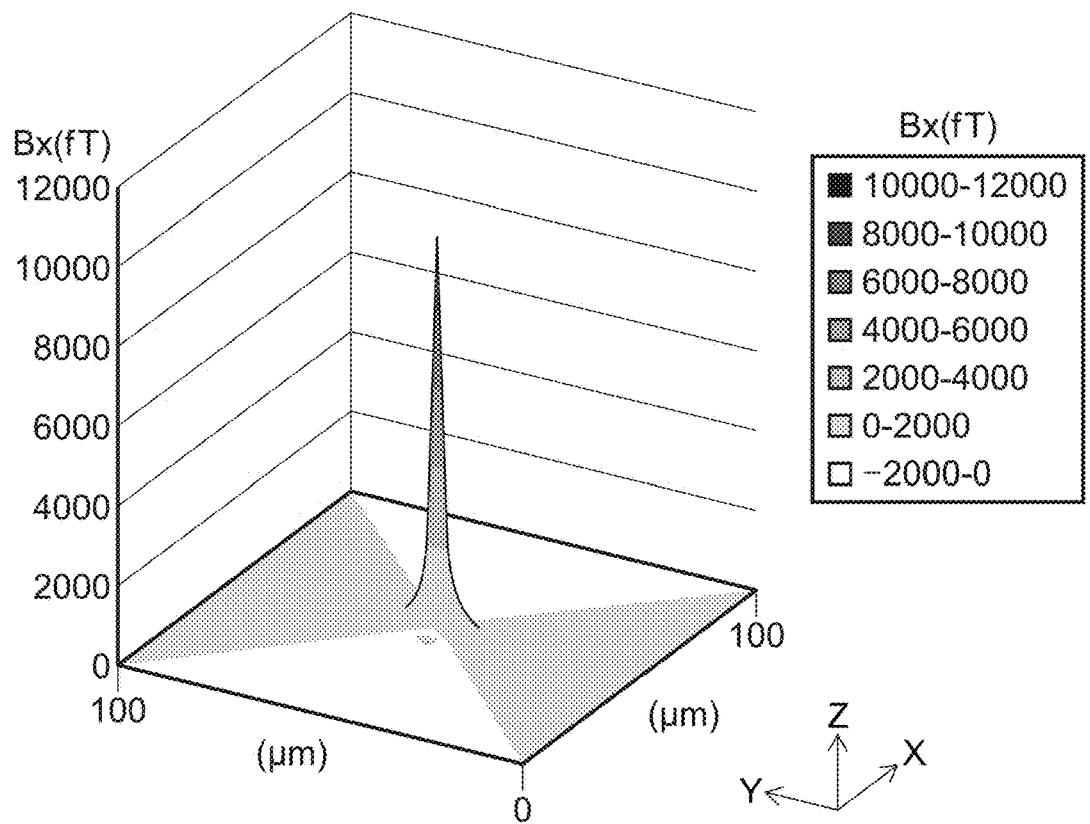

FIG. 6A and FIG. 6B are schematic views illustrating the simulation results.

These figures illustrate the spatial distribution of the magnetic field Bx when the distance d1 is 1 μm. The calculated region is a square of a side 100 μm. The spatial resolution of the calculation is 1 μm. The orientation of the current moment Mc is shown by an arrow. As shown in FIG. 6A and FIG. 6B, the peak of the strength of the magnetic field Bx is about 10000 fT (10 pT). Such a high magnetic field Bx is obtained within a range of about 1 μm. The size of the region (the region in the X-Y plane) where the high magnetic field is obtained is small.

Thus, in the case where the specimen 55 is a living body, etc., the spatial region that has the high magnetic field strength is small. Therefore, in the case where the number of the magnetic field sensors 20 is 1, slight change in the position of the magnetic field sensor 20 from the position of the specimen 55 makes the sensing difficult.

In the embodiment, by providing the multiple magnetic field sensors 20, for example, high-precision magnetic field sensing is possible even in the case where the specimen 55 is a living body. In the embodiment, for example, the multiple magnetic field sensors 20 are arranged two-dimensionally in the X-Y plane. For example, an arrangement having a matrix configuration is employed. Thereby, the activities in the entire specimen (cells or nerves) can be detected.

The second magnetic layer 20b has, for example, a soft magnetic property since the sensitivity of the change of the magnetization state to the magnetic field generated by the specimen 55 is high. The second magnetic layer 20b includes, for example, at least one of crystalline NiFe or crystalline FeCo. The second magnetic layer 20b includes, for example, amorphous CoZrB. In addition to the materials recited above, the second magnetic layer 20b may include other elements (e.g., additional elements).

For example, the second magnetization M2 of the second magnetic layer 20b is aligned with one direction when the magnetic field to be sensed is zero. For example, the second magnetic layer 20b has uniaxial magnetic anisotropy. For example, the second magnetic layer 20b may have shape magnetic anisotropy. For example, the second magnetic layer 20b may have magneto-crystalline anisotropy. The second magnetic layer 20b may be formed while applying a magnetic field. The second magnetic layer 20b may have exchange coupling interaction with a hard magnetic layer having a large coercivity. The second magnetic layer 20b may have exchange coupling interaction with an antiferromagnetic film. A leakage magnetic field from another magnetic body may be applied to the second magnetic layer 20b. Various methods may be used to control the second magnetization M2.

The first magnetic layer 20a may include, for example, a hard magnetic material. The direction of the magnetization of the hard magnetic material does not change easily by an external magnetic field. The first magnetic layer 20a may include, for example, a soft magnetic material. For example, a leakage magnetic field from another hard magnetic material may be applied to the soft magnetic material. The first magnetic layer 20a may include a stacked body including a hard magnetic material layer and a soft magnetic material layer. The first magnetic layer 20a may include a stacked body including an antiferromagnetic layer and a soft magnetic layer. Exchange coupling acts between the antiferromagnetic layer and the soft magnetic layer. In the first magnetic layer 20a, the magnetization of the soft magnetic material layer may be fixed in the magnetization direction of the antiferromagnetic layer.

For example, an exchange coupling interaction may act between the first magnetic layer 20a and the second magnetic layer 20b. A magnetostatic coupling interaction may act between the first magnetic layer 20a and the second magnetic layer 20b. The direction of the first magnetization M1 of the first magnetic layer 20a may be opposite to the direction of the second magnetization M2 of the second magnetic layer 20b. In that case, the change of the state (the rotation of the magnetization) of the second magnetization M2 of the second magnetic layer 20b induces a change (a rotation) of the state of the first magnetization M1 of the first magnetic layer 20a to the opposite direction. Then, the sensitivity to the magnetic field detection improves. For example, the thickness of the intermediate layer 20i (e.g., Ru, Ir, etc.) provided between the first magnetic layer 20a and the second magnetic layer 20b is thinner than 2 nm. Thereby, for example, an anti-parallel exchange coupling interaction is generated. For example, the first magnetic layer 20a and the second magnetic layer 20b may have anisotropic shape. Thereby, for example, a magnetostatic coupling force to the opposite direction is obtained.

For example, the multiple magnetic field sensors 20 may have a current-in-plane (CIP) GMR configuration. In such a case, for example, the intermediate layer 20i includes conductive materials such as Cu, etc.

The multiple magnetic field sensors 20 may have a current-perpendicular-to-plane TMR configuration. In such a case, the intermediate layer 20i includes an insulative material such as MgO, etc.

In CIP-GMR, the magnetoresistance ratio is small. However, noise at low frequency is low since the conductivity is high. In TMR, the magnetoresistance ratio is large. However, noise at low frequency is high since the conductivity is low.

Figure 7:
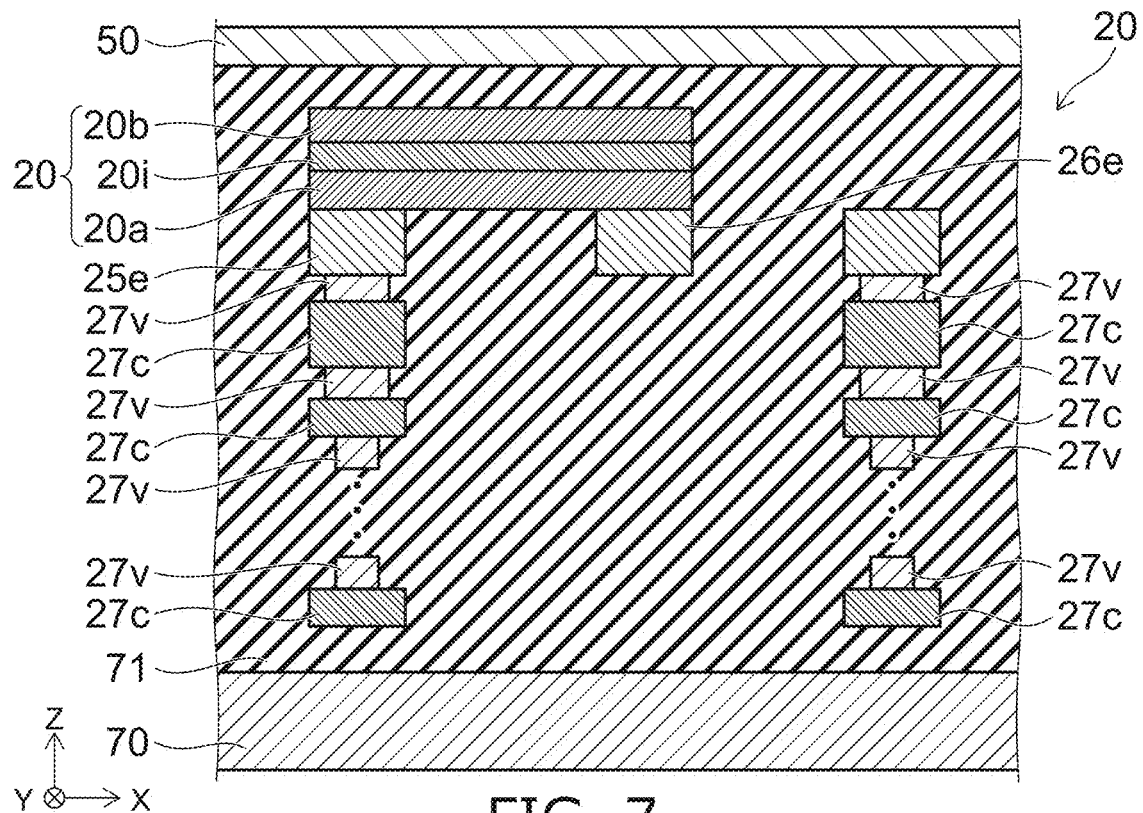
FIG. 7 is a schematic cross-sectional view illustrating a portion of the sensor according to the first embodiment.

FIG. 7 is a schematic cross-sectional view illustrating a portion of the sensor according to the first embodiment.

FIG. 7 illustrates one of the multiple magnetic field sensors 20. In the example, the magnetic field sensor 20 has a current-in-plane (CIP) GMR configuration. A first electrode 25e and a second electrode 26e are provided. The second electrode 26e is aligned with the first electrode 25e in a direction perpendicular to the Z-axis direction. The first magnetic layer 20a is provided between the nonmagnetic layer 50 and these electrodes. The second magnetic layer 20b is provided between the first magnetic layer 20a and the nonmagnetic layer 50. The first electrode 25e may be, for example, an interconnect. The second electrode 26e is, for example, a return electrode. In the example, interconnects 27c and vias 27v are provided between the base body 70 and the first electrode 25e. In the example, the multiple interconnects 27c are arranged in the Z-axis direction. The via 27v is provided between two interconnects 27c. The first electrode 25e is electrically connected to the interconnect 27c by the via 27v.

Figure 8:
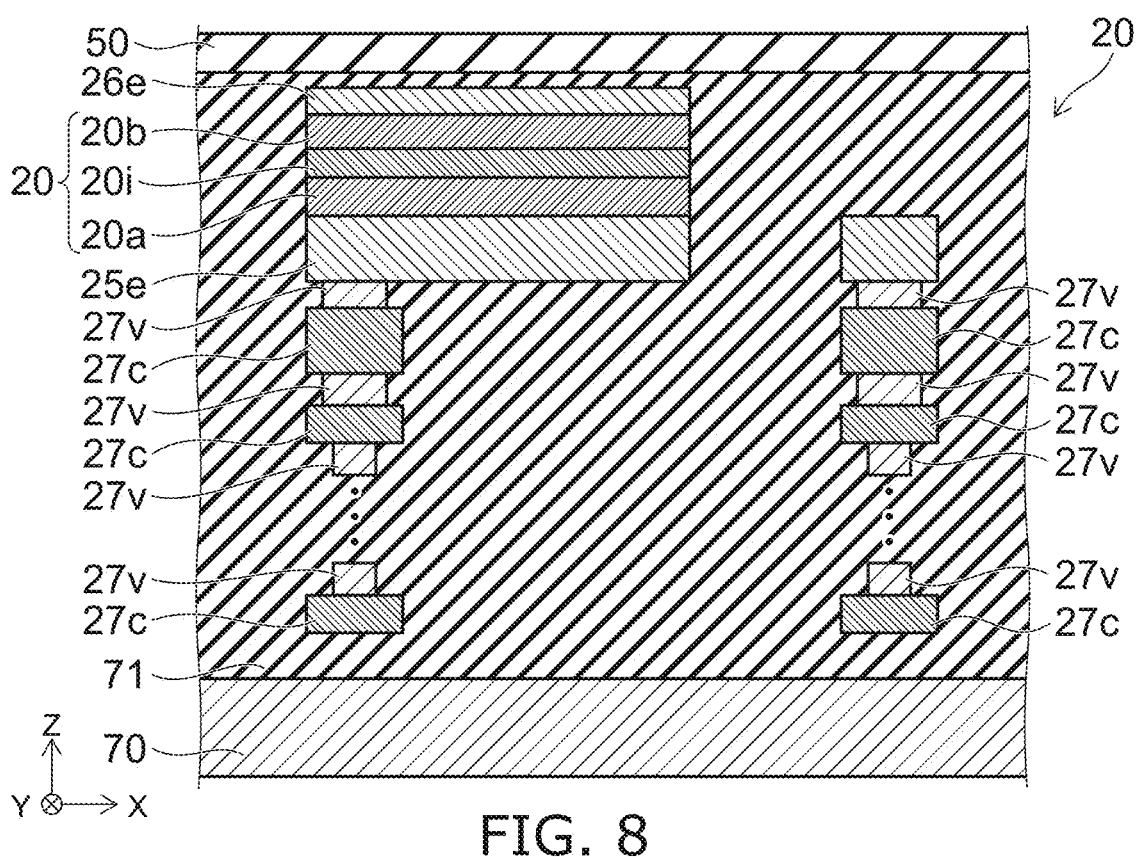
FIG. 8 is a schematic cross-sectional view illustrating a portion of the sensor according to the first embodiment.

FIG. 8 is a schematic cross-sectional view illustrating a portion of the sensor according to the first embodiment.

FIG. 8 shows another example of the multiple magnetic field sensors 20. In the example, the magnetic field sensor 20 is the TMR-type. The first magnetic layer 20a is provided between the first electrode 25e and the nonmagnetic layer 50. The second magnetic layer 20b is provided between the first magnetic layer 20a and the nonmagnetic layer 50. The second electrode 26e is provided between the second magnetic layer 20b and the nonmagnetic layer 50. The first electrode 25e may be, for example, an interconnect. In the example, the interconnects 27c and the vias 27v are provided between the base body 70 and the first electrode 25e. In the example, the multiple interconnects 27c are arranged in the Z-axis direction. The via 27v is provided between two interconnects 27c. The first electrode 25e is electrically connected to the interconnect 27c by the via 27v.

In the examples shown in FIG. 7 and FIG. 8, for example, the electrical resistance between the first electrode 25e and the second electrode 26e changes according to the activities in the specimen 55. For example, a signal that corresponds to an electrical pulse signal in the specimen 55 can be obtained between an interconnect connected to the first electrode 25e and an interconnect connected to the second electrode 26e.

Several examples of magnetic field sensors will now be described.

FIG. 9A to FIG. 9E are schematic cross-sectional views illustrating portions of the sensor according to the embodiment.

These drawings show examples of the multiple magnetic field sensors 20.

Figure 9A:
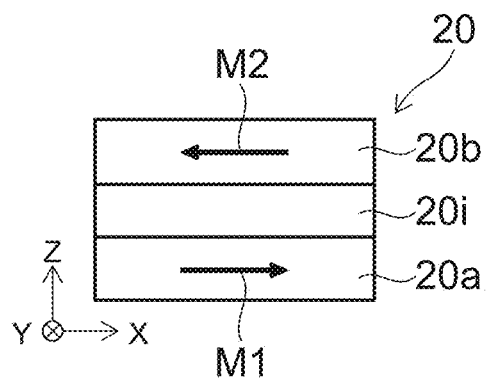
FIG. 9A to FIG. 9E are schematic cross-sectional views illustrating portions of the sensor according to the embodiment.

In the example shown in FIG. 9A, the intermediate layer 20i is provided between the first magnetic layer 20a and the second magnetic layer 20b. In the example, the intermediate layer 20i is a nonmagnetic conductive layer. In the example, the first magnetic layer 20a and the second magnetic layer 20b are antiferromagnetically coupled via the intermediate layer 20i. For example, when a magnetic field is not substantially applied to the magnetic field sensor 20, the direction of the first magnetization M1 of the first magnetic layer 20a is opposite to the direction of the second magnetization M2 of the second magnetic layer 20b.

In the example, the first magnetic layer 20a, the second magnetic layer 20b, and the intermediate layer 20i are rectangles. The length in one direction (e.g., the major axis) of the rectangle is longer than the length in another direction (e.g., the minor axis). For example, the magnetization of each of these magnetic layers is aligned with the rectangle major axis. For example, the magnetic field sensor 20 of the example has a scissors-type CIP-GMR configuration. For example, the angle between the directions of the magnetizations of these magnetic layers changes according to the applied magnetic field.

The nonmagnetic conductive layer that is used as the intermediate layer 20i includes, for example, at least one of Cu, Ru, or Ir. The thickness of the intermediate layer 20i is, for example, 2 nm or less. Thereby, for example, antiferromagnetic exchange coupling is induced.

In the embodiment, the magnetization of at least one of the first magnetic layer 20a or the second magnetic layer 20b may be aligned with the rectangle minor axis. For example, such a configuration is obtained by a fabrication process such as cooling in a magnetic field, etc. For example, the angle between the two magnetizations may be less than 180 degrees when a magnetic field is substantially not applied to the magnetic field sensor 20. In this case, high sensitivity to the applied magnetic field is obtained.

In the embodiment, at least one of the first magnetic layer 20a or the second magnetic layer 20b includes, for example, an FeCo alloy. At least one of the first magnetic layer 20a or the second magnetic layer 20b may include, for example, a Heusler alloy. In this case, high magneto-resistance ratio is obtained due to high spin polarization.

For example, the leakage magnetic field from the first magnetic layer 20a may be applied to the second magnetic layer 20b. For example, the leakage magnetic field from the second magnetic layer 20b may be applied to the first magnetic layer 20a.

Figure 9B:
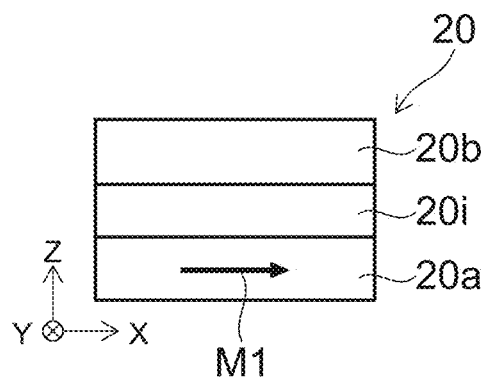

In one of the multiple magnetic field sensors 20 as shown in FIG. 9B, the first magnetization M1 of the first magnetic layer 20a is substantially fixed. The first magnetic layer 20a is, for example, a reference layer. On the other hand, the second magnetic layer 20b is a free layer. For example, the magnetic field sensor 20 may have a spin-valve type GMR configuration. The first magnetic layer 20a, the second magnetic layer 20b, and the intermediate layer 20i are rectangles.

For example, the first magnetic layer 20a has magneto-crystalline anisotropy and shape magnetic anisotropy. Thereby, the first magnetization M1 is substantially fixed. For example, the first magnetization M1 is aligned with the rectangle major axis.

In the example as well, the magnetization of at least one of the first magnetic layer 20a or the second magnetic layer 20b may be aligned with the rectangle minor axis. For example, the angle between the two magnetizations may be less than 180 degrees when a magnetic field substantially is not applied to the magnetic field sensor 20. In this case, high sensitivity is obtained.

In the example as well, at least one of the first magnetic layer 20a or the second magnetic layer 20b may include, for example, at least one of an FeCo alloy or a Heusler alloy. Since high spin polarization is obtained, a high magneto-resistance ratio is expected.

The first magnetic layer 20a may include, for example, at least one of a CoPt alloy or a CoPd alloy. The first magnetic layer 20a may include, for example, at least one of an ordered phase alloy of FePt, an ordered phase alloy of CoP, or an ordered phase alloy of CoPd. The first magnetic layer 20a may include at least one of an artificial lattice film of Co/Pd, an artificial lattice film of Co/Pt, or an artificial lattice film of Co/Ni. In these cases, a high magneto-crystalline anisotropy is obtained.

Figure 9C:
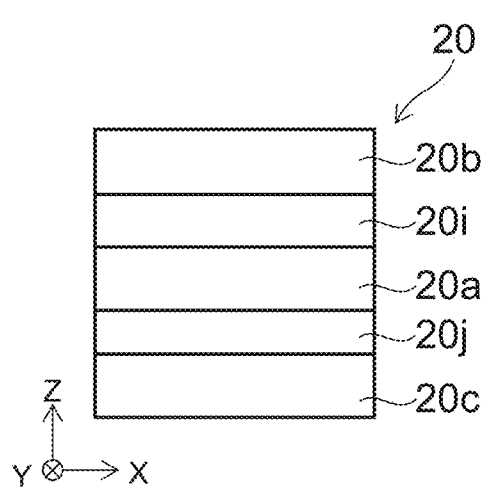

In the example shown in FIG. 9C, one of the multiple magnetic field sensors 20 further includes a third magnetic layer 20c and a nonmagnetic layer 20j in addition to the first magnetic layer 20a, the second magnetic layer 20b, and the intermediate layer 20i. The first magnetic layer 20a is provided between the third magnetic layer 20c and the second magnetic layer 20b. The nonmagnetic layer 20j is provided between the third magnetic layer 20c and the first magnetic layer 20a. The nonmagnetic layer 20j includes, for example, Ru. The thickness of the nonmagnetic layer 20j is, for example, 2 nm or less. The third magnetic layer 20c is, for example, an antiferromagnetic layer. For example, the magnetization of the first magnetic layer 20a is substantially fixed by the third magnetic layer 20c. In the example, the nonmagnetic layer 20j may be omitted.

The third magnetic layer 20c includes, for example, IrMn. Thereby, for example, a stable antiferromagnetic state can be obtained.

In the example shown in FIG. 9A to FIG. 9C, the intermediate layer 20i may be nonmagnetic and insulative. The magnetic field sensor 20 may have a current-perpendicular-to-plane TMR configuration. The intermediate layer 20i includes, for example, at least one of MgO or TiO. The intermediate layer 20i may include these materials and other elements (additional elements).

Figure 9D:
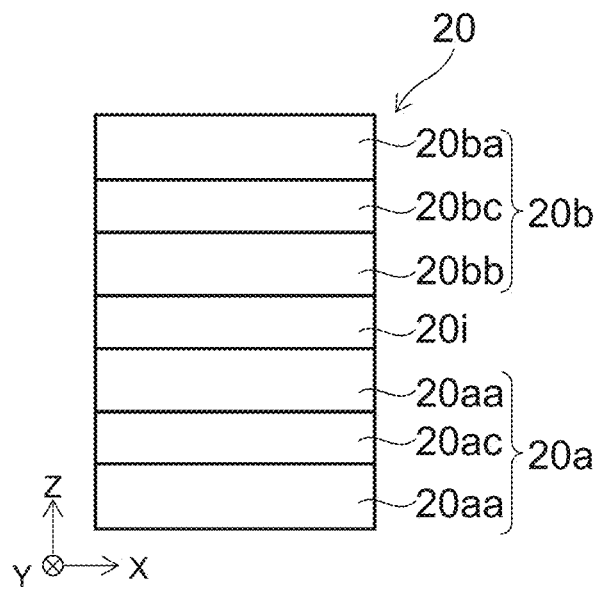

In the example shown in FIG. 9D, the first magnetic layer 20a includes a first high electrical resistance layer 20aa, a first low electrical resistance layer 20ab, and a first nonmagnetic layer 20ac. The first low electrical resistance layer 20*ab* is provided between the first high electrical resistance layer 20*aa* and the intermediate layer 20*i*. The first nonmagnetic layer 20*ac* is provided between the first high electrical resistance layer 20*aa* and the first low electrical resistance layer 20*ab*. For example, the first low electrical resistance layer 20*ab* contacts the intermediate layer 20*i*.

The second magnetic layer 20*b* includes a second high electrical resistance layer 20*ba*, a second low electrical resistance layer 20*bb*, and a second nonmagnetic layer 20*bc*. The second low electrical resistance layer 20*bb* is provided between the second high electrical resistance layer 20*ba* and the intermediate layer 20*i*. The second nonmagnetic layer 20*bc* is provided between the second high electrical resistance layer 20*ba* and the second low electrical resistance layer 20*bb*. For example, the second low electrical resistance layer 20*bb* contacts the intermediate layer 20*i*.

The first high electrical resistance layer 20*aa*, the first low electrical resistance layer 20*ab*, the second high electrical resistance layer 20*ba*, and the second low electrical resistance layer 20*bb* include, for example, soft magnetic materials. The first nonmagnetic layer 20*ac* and the second nonmagnetic layer 20*bc* include, for example, Ru.

For example, the first high electrical resistance layer 20*aa* and the first low electrical resistance layer 20*ab* have antiferromagnetic exchange coupling with each other. For example, the second high electrical resistance layer 20*ba* and the second low electrical resistance layer 20*bb* have antiferromagnetic exchange coupling with each other. In the example, the intermediate layer 20*i* is conductive. A CIP-GMR configuration is applied.

In the example, by employing the configuration recited above, scattering of the conduction electrons at the interfaces of the layers increases. By providing the high electrical resistance layer, the current that flows through the high electrical resistance layer can be suppressed. Thus, a high magneto-resistance ratio is obtained. By providing the high electrical resistance layer and the low electrical resistance layer in the first magnetic layer 20*a* and the second magnetic layer 20*b*, the magnetization in these layers rotate as a unified magnetic layer. Therefore, the magnetic volume becomes large, and the thermal fluctuation noise can be reduced.

In the example, the soft magnetic low electrical resistance layer includes, for example, at least one of an FeCo alloy or a Heusler alloy. Since the spin polarization at the interface with the nonmagnetic intermediate layer 20*i* is high, a high magnetoresistance ratio is expected.

In the example, the soft magnetic high electrical resistance layer includes, for example, at least one of CoFeSi, CoFeSiB, CoZrNb, or CoFeB. The soft magnetic high electrical resistance layer includes, for example, an amorphous alloy of these materials. Thus, good soft magnetic properties can be obtained.

Figure 9E:
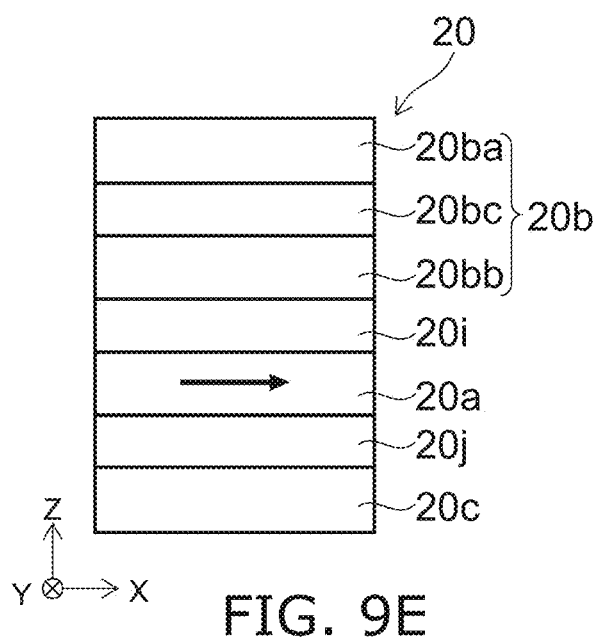

In the example shown in FIG. 9E, one of the multiple magnetic field sensors 20 further includes the third magnetic layer 20*c* and the nonmagnetic layer 20*j* described in reference to FIG. 9C in addition to the first magnetic layer 20*a*, the second magnetic layer 20*b*, and the intermediate layer 20*i*. The second magnetic layer 20*b* includes the second high electrical resistance layer 20*ba*, the second low electrical resistance layer 20*bb*, and the second nonmagnetic layer 20*bc*. In other words, the configuration described in reference to FIG. 9D is applied to the second magnetic layer 20*b*.

Thus, in the embodiment, various modifications of the multiple magnetic field sensors 20 are possible.

FIG. 10A to FIG. 10H are schematic plan views illustrating portions of the sensor according to the first embodiment.

These drawings illustrate some of the multiple magnetic field sensors 20.

Figure 10A:
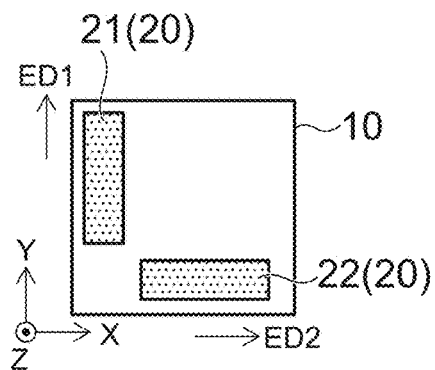
FIG. 10A to FIG. 10H are schematic plan views illustrating portions of the sensor according to the first embodiment.

As shown in FIG. 10A, the multiple magnetic field sensors 20 include a first magnetic field sensor 21 and a second magnetic field sensor 22. The length along one direction is longer than the length along another direction for each of the magnetic field sensors 20.

For example, the length of the first magnetic field sensor 21 along a first extension direction ED1 is longer than the length of the first magnetic field sensor 21 along a direction perpendicular to the first extension direction ED1. The first extension direction ED1 and the direction recited above that is perpendicular to the first extension direction ED1 are aligned with the second surface 50*b* (referring to FIG. 1B). The first extension direction ED1 is, for example, the major-axis direction of the first magnetic field sensor 21.

On the other hand, the length of the second magnetic field sensor 22 along a second extension direction ED2 is longer than the length of the second magnetic field sensor 22 along a direction perpendicular to the second extension direction ED2. The second extension direction ED2 and the direction recited above that is perpendicular to the second extension direction ED2 are aligned with the second surface 50*b*. The second extension direction ED2 crosses the first extension direction ED1. The second extension direction ED2 is, for example, the major-axis direction.

In the example, the angle between the first extension direction ED1 and the second extension direction ED2 is not less than 80 degrees and not more than 100 degrees. In the embodiment, this angle may be greater than 0 degrees and less than 180 degrees.

By setting the directions in which the two magnetic field sensors 20 extend to cross, a magnetic field in any direction can be sensed.

In the example, the first magnetic field sensor 21 and the second magnetic field sensor 22 are provided in one sensing component 10. In the embodiment, the number of the multiple magnetic field sensors 20 provided may be three or more.

Figure 10B:
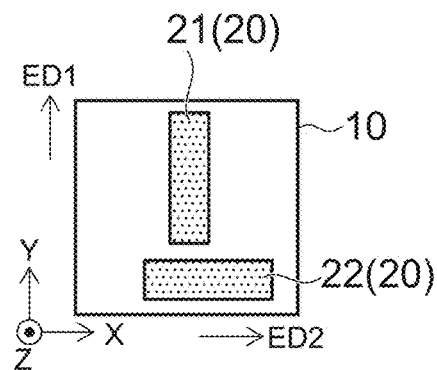

As shown in FIG. 10B, the positions of the magnetic field sensors 20 inside the one sensing component 10 are arbitrary.

Figure 10C:
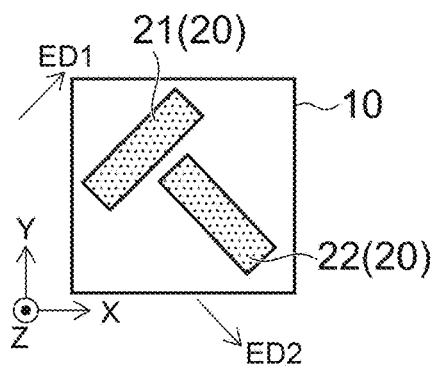

As shown in FIG. 10C, the first extension direction ED1 and the second extension direction ED2 are tilted with respect to the X-axis direction. The angle of the tilt is about 45 degrees (e.g., not less than 40 degrees and not more than 50 degrees).

Figure 10D:
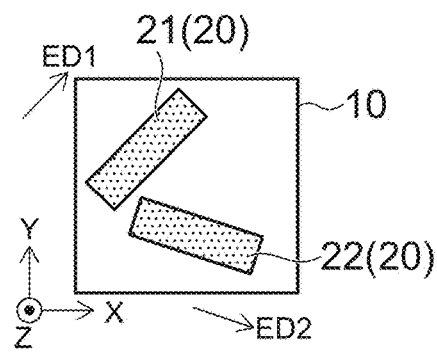
Figure 10E:
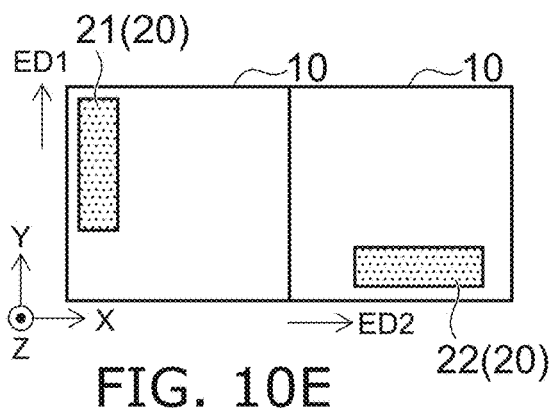
Figure 10F:
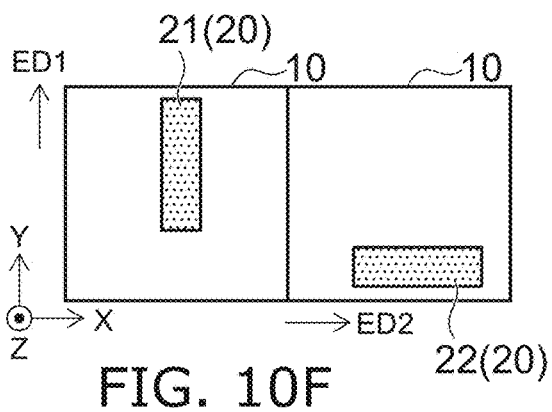
Figure 10G:
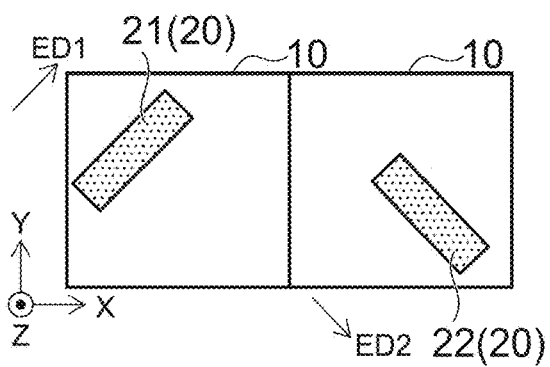
Figure 10H:
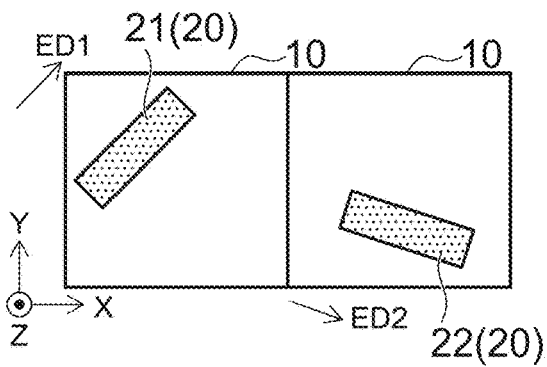

As shown in FIG. 10D, the angle between the first extension direction ED1 and the second extension direction ED2 is about 45 degrees (e.g., not less than 20 degrees and not more than 60 degrees).

In the example shown in FIG. 10E to FIG. 10H, the first magnetic field sensor 21 and the second magnetic field sensor 22 described in reference to FIG. 10A are provided. In the example, the first magnetic field sensor 21 is provided in one sensing component 10. The second magnetic field sensor 22 is provided in one other sensing component 10.

In the example shown in FIG. 10A to FIG. 10H, at least two of the multiple magnetic field sensors 20 may be connected to one interconnect. For example, power source lines of at least two of the multiple magnetic field sensors 20 may be common. In this case, configuration is simpler.

Figure 11A:
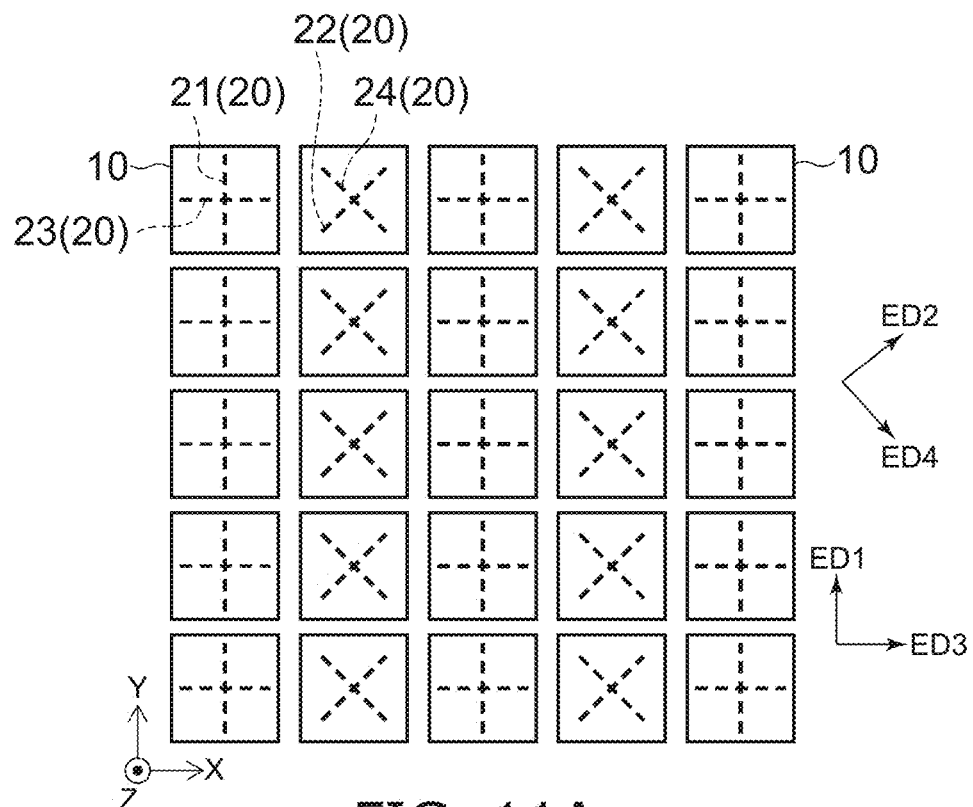
FIG. 11A and FIG. 11B are schematic plan views illustrating portions of the sensor according to the first embodiment.
Figure 11B:
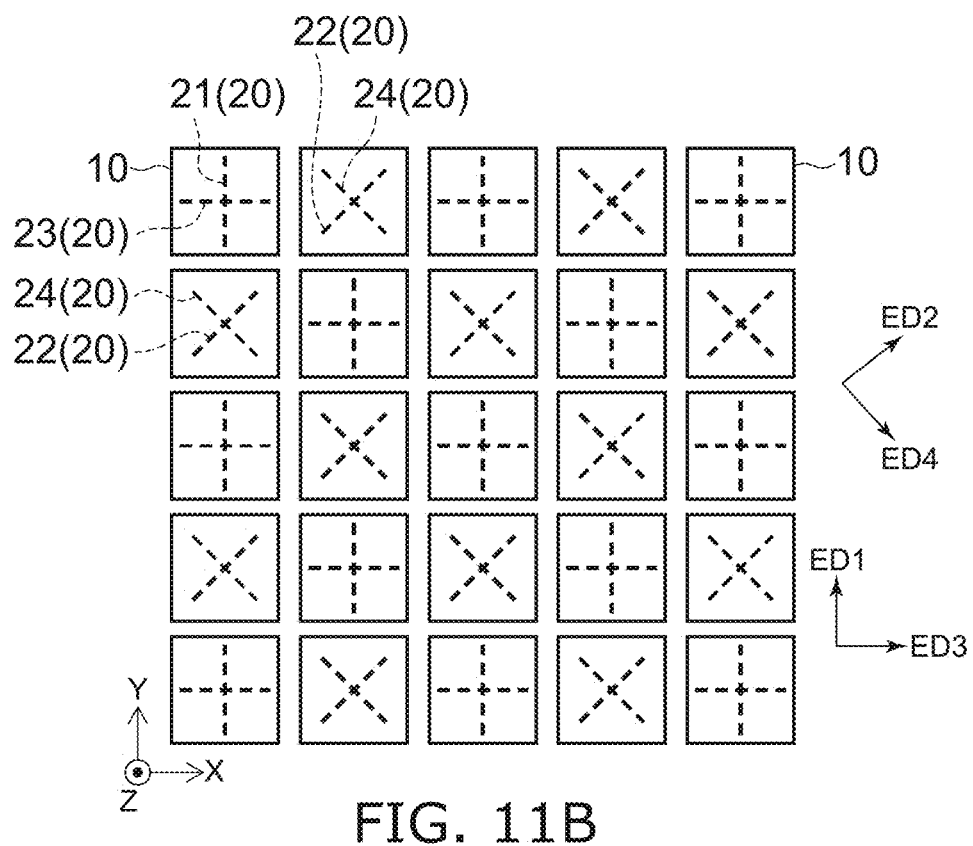

FIG. 11A and FIG. 11B are schematic plan views illustrating portions of the sensor according to the first embodiment.

These drawings illustrate some of the multiple magnetic field sensors 20.

As shown in FIG. 11A, the multiple magnetic field sensors 20 include the first magnetic field sensor 21 and the second magnetic field sensor 22. The second extension direction ED2 of the second magnetic field sensor 22 crosses the first extension direction ED1 of the first magnetic field sensor 21. The multiple magnetic field sensors 20 further include a third magnetic field sensor 23 and a fourth magnetic field sensor 24. A fourth extension direction ED4 of the fourth magnetic field sensor 24 crosses a third extension direction ED3 of the third magnetic field sensor 23. In the example, the first magnetic field sensor 21 and the third magnetic field sensor 23 are provided inside one sensing component 10. The second magnetic field sensor 22 and the fourth magnetic field sensor 24 are provided inside one other sensing component 10.

Multiple first magnetic field sensors 21 are provided. Multiple second magnetic field sensors 22 are provided. One of the multiple second magnetic field sensors 22 is disposed between two of the multiple first magnetic field sensors 21. One of the multiple first magnetic field sensors 21 is disposed between two of the multiple second magnetic field sensors 22.

Multiple third magnetic field sensors 23 are provided. Multiple fourth magnetic field sensors 24 are provided. One of the multiple fourth magnetic field sensors 24 is disposed between two of the multiple third magnetic field sensors 23. One of the multiple third magnetic field sensors 23 is disposed between two of the multiple fourth magnetic field sensors 24.

In the example of FIG. 11A, the multiple first magnetic field sensors 21 and the multiple second magnetic field sensors 22 are arranged along the X-axis direction. The multiple third magnetic field sensors 23 and the multiple fourth magnetic field sensors 24 are arranged along the X-axis direction.

In the example shown in FIG. 11B, the multiple first magnetic field sensors 21 and the multiple second magnetic field sensors 22 are arranged along the X-axis direction and further arranged in the Y-axis direction. The multiple third magnetic field sensors 23 and the multiple fourth magnetic field sensors 24 are arranged along the X-axis direction and further arranged along the Y-axis direction.

In the embodiment, various modifications of the arrangement of the multiple first to fourth magnetic field sensors 21 to 24 are possible.

In the embodiment, for example, the first magnetic layer 20a is a reference layer; and the second magnetic layer 20b is a free layer. For example, the magnetic volume (Ms1·t1) of the first magnetic layer 20a is smaller than the magnetic volume (Ms2·t2) of the second magnetic layer 20b. For example, the product of the thickness t1 of the first magnetic layer 20a and a saturation magnetization Ms1 of the first magnetic layer 20a is smaller than the product of the thickness t2 of the second magnetic layer 20b and a saturation magnetization Ms2 of the second magnetic layer 20b.

In the embodiment, the base body 70 (referring to FIG. 1B) may include, for example, a semiconductor substrate (e.g., a silicon substrate, etc.). For example, the base body 70 may include a circuit of CMOS, etc. The base body 70 may include, for example, a compound semiconductor substrate of GaAs, etc. The base body 70 may include a semiconductor substrate, and an insulating layer (a $SiO_2$ layer, etc.) provided on the semiconductor substrate. The base body 70 may include, for example, a single crystal substrate of MgO, AlO, etc. The base body 70 may include a substrate of C, SiC, etc. The base body 70 may include a soft material such as PDMS (polydimethylsiloxane).

The insulating layer 71 (referring to FIG. 1B) includes, for example, at least one of $SiO_2$ or SiN. The insulating layer 71 may include, for example, a metal oxide, a metal nitride, or a metal oxynitride. The insulating layer 71 is provided around these components in the case where a metal interconnect, a semiconductor element, a protective layer, an under layer, or the like is provided between the nonmagnetic layer 50 and the base body 70.

For example, the front surface of the nonmagnetic layer 50 (referring to FIG. 1B) has affinity with the specimen 55. In the case where the specimen 55 includes a cell, the nonmagnetic layer 50 includes at least one of $SiO_2$ or SiN. For example, the movement of ions (e.g., Cu ions, etc.) toward the specimen 55 side is suppressed. For example, the front surface of the nonmagnetic layer 50 may have a configuration having a hexagonal close-packed nanostructure; and, for example, the configuration may be formed by self assembly. The efficiency of the cell culture is increased by such a configuration. The nonmagnetic layer 50 may include at least one of silicon oxide, aluminum oxide, or tantalum oxide.

A partition (described below) may be provided on the front surface of the nonmagnetic layer 50. For example, leakage of the retaining liquid of the cell can be suppressed by the partition. For example, the partition may be provided for each of the multiple sensing components 10. For example, the partition may be provided for the multiple sensing components 10. The partition may be provided at the peripheral edge portion of the sensor.

Second Embodiment

Figure 12A:
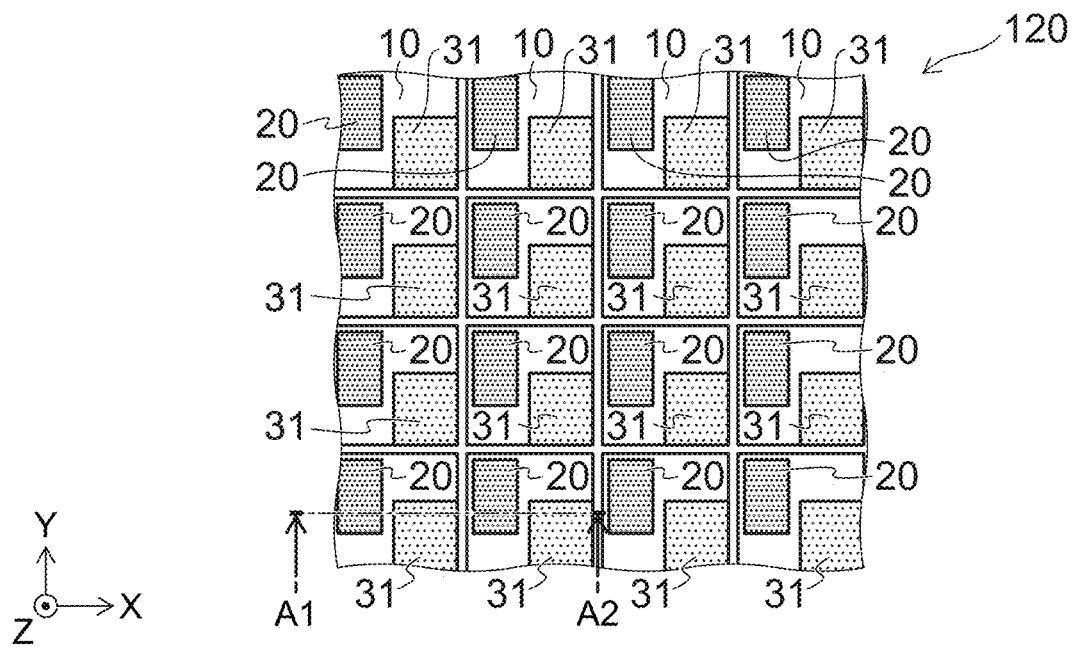
FIG. 12A and FIG. 12B are schematic views illustrating a sensor according to a second embodiment.
Figure 12B:
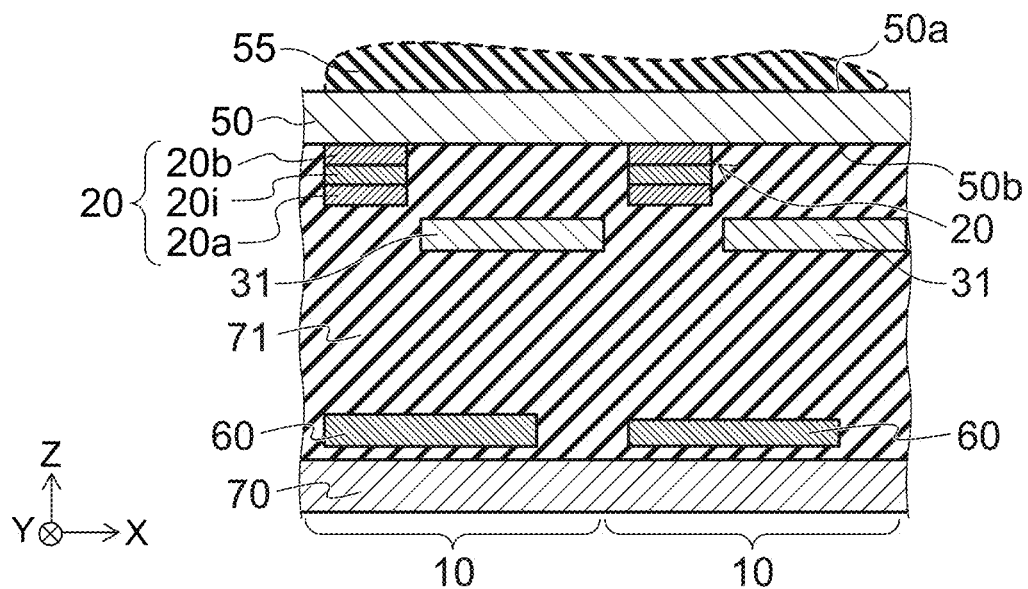

FIG. 12A and FIG. 12B are schematic views illustrating a sensor according to a second embodiment.

FIG. 12A is a plan view. FIG. 12B is a cross-sectional view of FIG. 12A along the line A1-A2.

As shown in FIG. 12A and FIG. 12B, the sensor 120 according to the embodiment further includes multiple optical sensors 31 in addition to the nonmagnetic layer 50 and the multiple magnetic field sensors 20 described in reference to the first embodiment. The multiple optical sensors 31 are arranged along the second surface 50b of the nonmagnetic layer 50.

For example, at least one of the multiple magnetic field sensors 20 and at least one of the multiple optical sensors 31 are included in one of the multiple sensing components 10.

As shown in FIG. 12B, for example, the distance between the first surface 50a and the at least one of the multiple magnetic field sensors 20 recited above is shorter than the distance between the first surface 50a and the at least one of the multiple optical sensors 31 recited above. For example, the at least one of the multiple magnetic field sensors 20 recited above may be positioned between the nonmagnetic layer 50 and the at least one of the multiple optical sensors 31 recited above in the Z-axis direction.

In the sensor 120, the distance d1 between the first surface 50a and the second magnetic layer 20b is 10 μm or less. Then, high SNR is obtained. Also, high spatial resolution and/or high temporal resolution are obtained. In the sensor 120, information for multiple characteristics (multi-item) can be obtained by using optical information in addition to the information based on the magnetic field. The activities in the specimen 55 can be sensed more accurately.

In the sensor 120, for example, the multiple sensing components 10 are arranged in a matrix configuration. One of the multiple sensing components 10 includes multiple sensor elements (the magnetic field sensor 20, the optical sensor 31, etc.). For example, the multiple sensing components 10 are used as a sensor pixel array. The sensor circuit portion 60 is provided in the sensor 120 as well. The sensor circuit portion 60 includes, for example, a selection circuit of the multiple sensing components 10, a read circuit of the multiple sensing components 10, and a current supply circuit for the multiple sensing components 10. The nonmagnetic layer 50 is transmissive to the wavelengths of light sensed by the multiple optical sensors 31.

For example, one of the multiple sensing components 10 corresponds to one pixel. For example, the information obtained from the multiple sensors included in the multiple sensing components 10 may be processed as integrated information. For example, optical image of the specimen 55 and the signal generated from the specimen 55 may be processed as an image data that changes temporally. For example, the image is displayed. For example, the image is processed.

The multiple optical sensors 31 include, for example, photodiodes. The optical sensors 31 may further include optical filters. The optical filters may include, for example, multilayer films; and the multilayer films include, for example, inorganic films or organic films. The designated wavelength of light from the object can be detected by using the optical filters. For example, the interconnects, etc., that overlap the optical sensor 31 may be light-transmissive. The interconnects include, for example, ITO, etc.

Figure 13:
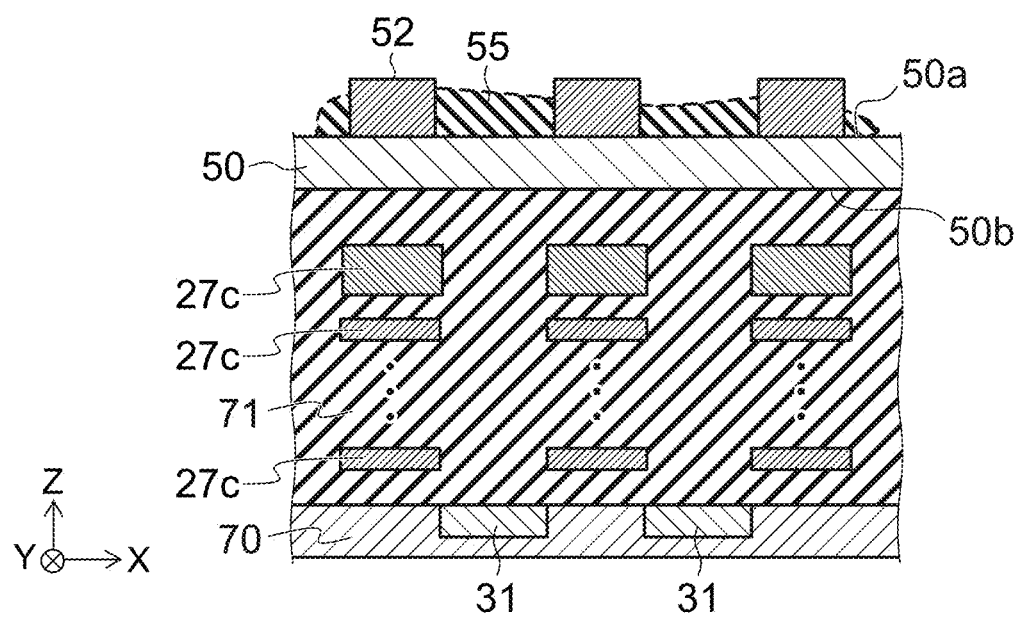
FIG. 13 is a schematic cross-sectional view illustrating a portion of the sensor according to the second embodiment.

FIG. 13 is a schematic cross-sectional view illustrating a portion of the sensor according to the second embodiment.

FIG. 13 illustrates the optical sensors 31. For example, the multiple optical sensors 31 are provided at a portion on the upper side of the base body 70. The optical sensors 31 include, for example, photodiodes. The interconnects 27c are provided in the example. For example, the optical sensors 31 and at least a portion of the interconnects 27c do not overlap each other in the Z-axis direction. A partition 52 is provided in the example. The nonmagnetic layer 50 is provided between the base body 70 and the partition 52. In the example, the partition 52 and the interconnects 27c overlap each other in the Z-axis direction. The optical sensors 31 and at least a portion of the partition 52 do not overlap each other in the Z-axis direction.

Figure 14A:
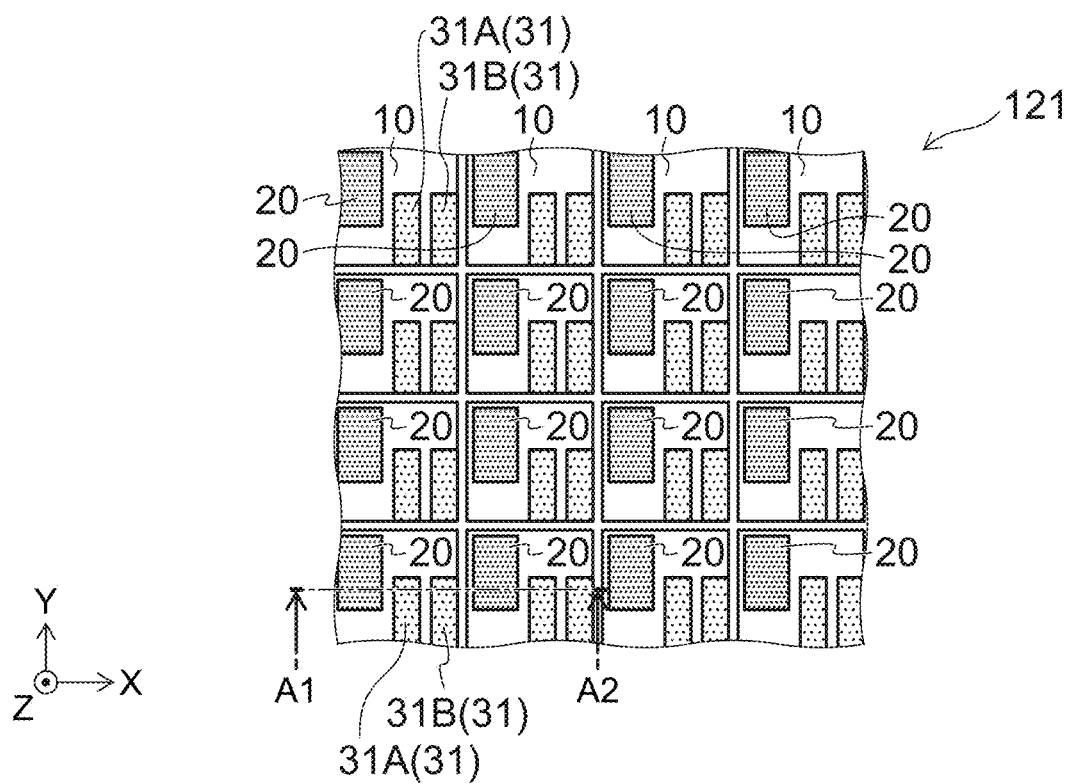
FIG. 14A and FIG. 14B are schematic views illustrating another sensor according to the second embodiment.
Figure 14B:
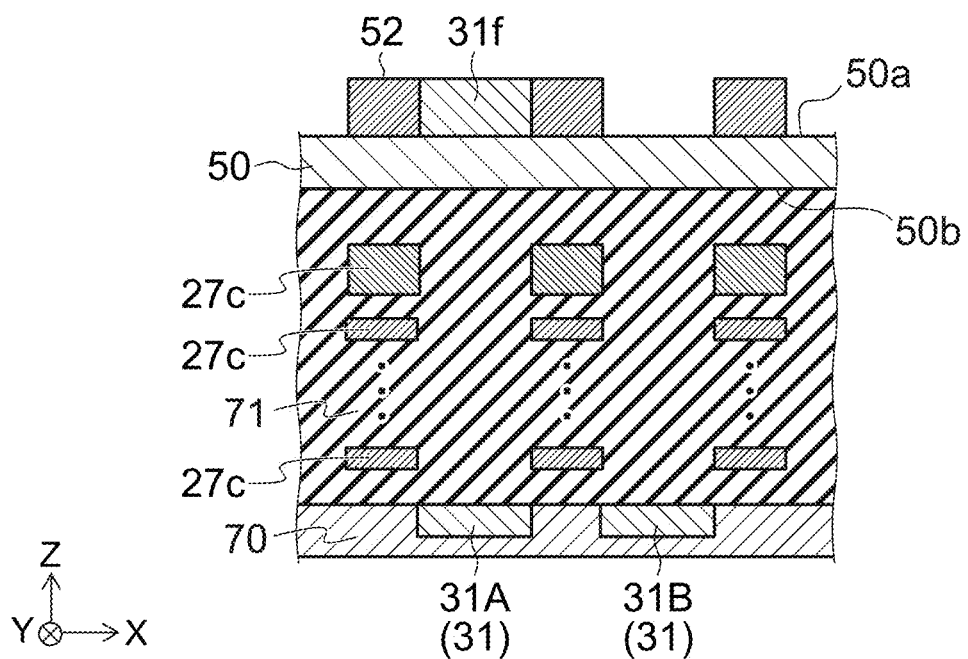

FIG. 14A and FIG. 14B are schematic views illustrating another sensor according to the second embodiment.

FIG. 14A is a plan view. FIG. 14B is a cross-sectional view illustrating a portion of the sensor.

In the other sensor 121 according to the embodiment as shown in FIG. 14A, the multiple optical sensors 31 are provided in one sensing component 10. The multiple optical sensors 31 include, for example, a first optical sensor 31A and a second optical sensor 31B.

An optical filter 31f is provided as shown in FIG. 14B. The optical filter 31f and the first optical sensor 31A overlap each other in the Z-axis direction. The optical filter 31f and the second optical sensor 31B do not overlap each other in the Z-axis direction.

For example, the optical filter 31f includes multiple films having, for example, mutually-different refractive indexes. The multiple films are arranged alternately in the Z-axis direction. The multiple films are, for example, inorganic films. One of the multiple films includes, for example, a silicon oxide film. One other of the multiple films includes, for example, zirconium oxide. The optical filter 31f may include at least one of a pigment or a dye. The position in the Z-axis direction where the optical filter 31f is provided is arbitrary.

By providing the optical filter 31f, for example, the fluorescence that is generated by reacting with a designated protein can be sensed with a high SNR. For example, the wavelength of an external light noise can be suppressed.

One of the multiple optical sensors 31 and one of the multiple optical filters 31f may overlap in the Z-axis direction; and one other of the multiple optical sensors 31 and one other of the multiple optical filters 31f may overlap in the Z-axis direction. In such a case, for example, the optical characteristics of the one of the multiple optical filters 31f recited above are different from the optical characteristics of the one other of the multiple optical filters 31f recited above.

In the example of FIG. 14B, for example, the image of the specimen 55 can be obtained by the second optical sensor 31B that does not overlap the optical filter 31f.

As in the sensor 121, the multiple optical sensors 31 may be provided in one sensing component 10. The optical characteristics of the multiple optical sensors are different from each other. In the example, the existence or absence of the optical filter 31f is different. The optical characteristics of the optical filters 31f may be set to be different from each other. For example, the specimen 55 may be sensed using a substance that emits a designated fluorescence by reacting to designated ions or proteins. For example, the activity in the specimen 55 (e.g., at least one of an absorption or a discharge of the ions or the protein) can be sensed as an image with spatial distribution that changes with time. By providing the multiple optical sensors 31 with different optical characteristics, such sensing capability can be implemented efficiently. In addition to the real shape image of the specimen 55 that utilizes at least one of the scattered light or the transmitted light via the specimen 55, the activities in the specimen 55 can be sensed more accurately by using such sensing.

Figure 15:
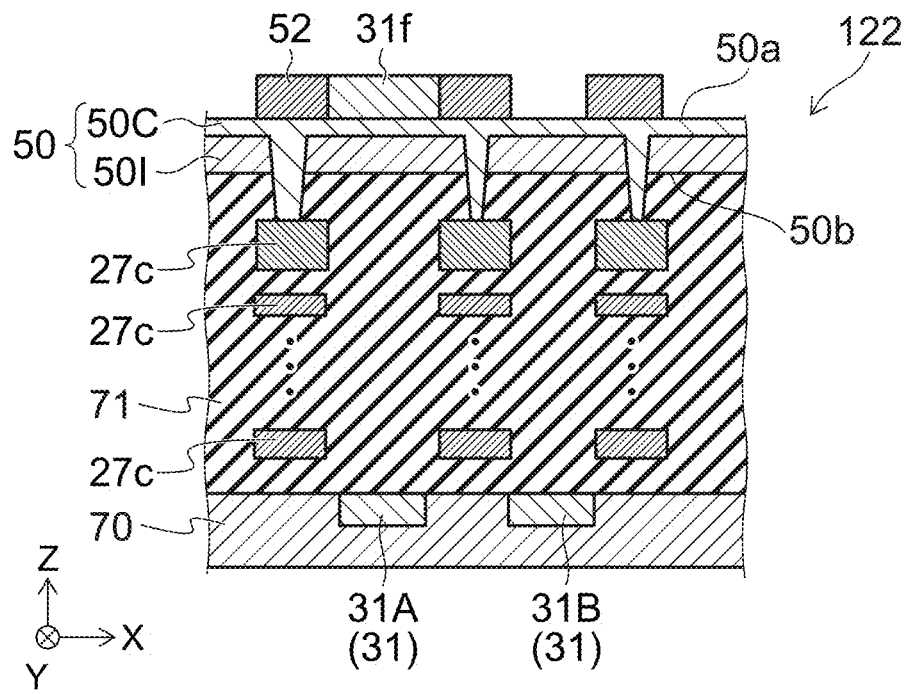
FIG. 15 is a schematic cross-sectional view illustrating a portion of another sensor according to the second embodiment.

FIG. 15 is a schematic cross-sectional view illustrating a portion of another sensor according to the second embodiment.

In the sensor 122 as shown in FIG. 15, the nonmagnetic layer 50 includes an insulating layer 501 and a conductive layer 50C. The insulating layer 501 is provided between the interconnects 27c and at least a portion of the conductive layer 50C in the Z-axis direction. A portion of the conductive layer 50C extends in the Z-axis direction through the insulating layer 501 and is electrically connected to the interconnects 27c. The insulating layer 501 includes, for example, SiN. The conductive layer 50C includes, for example, a metal oxide (ITO, InGaZnO, $TiO_2$, etc.). The conductive layer 50C is light-transmissive.

For example, electrophoresis of the specimen 55 may be caused by the conductive layer 50C. The specimen 55 may be guided by the conductive layer 50C. Electrical stimulation may be applied to the specimen 55 by the conductive layer 50C. The light that is irradiated to the specimen 55 may be sensed by the optical sensors 31. Simultaneously with the sensing by the optical sensors 31, an electrical signal (a voltage signal, a potential signal, etc.) of the specimen 55 may be measured.

Figure 16:
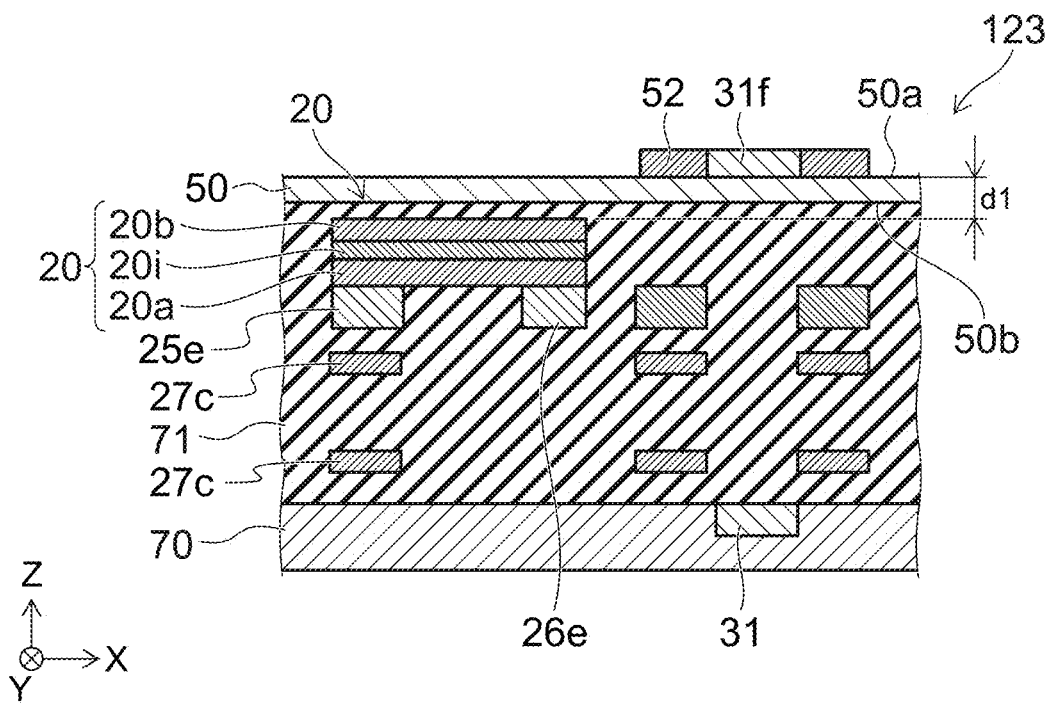
FIG. 16 is a schematic cross-sectional view illustrating a portion of another sensor according to the second embodiment.

FIG. 16 is a schematic cross-sectional view illustrating a portion of another sensor according to the second embodiment.

In the sensor 123 as shown in FIG. 16, the first magnetic layer 20a, the second magnetic layer 20b, and the intermediate layer 20i are provided between the first electrode 25e, the second electrode 26e, and the nonmagnetic layer 50. For example, the magnetic field sensor 20 has a CIP-GMR configuration. The optical filter 31f is provided on the optical sensor 31.

An example of a method for manufacturing the sensor 123 will now be described.

FIG. 17A to FIG. 17C, FIG. 18A, and FIG. 18B are schematic cross-sectional views illustrating the method for manufacturing the sensor according to the second embodiment.

Figure 17A:
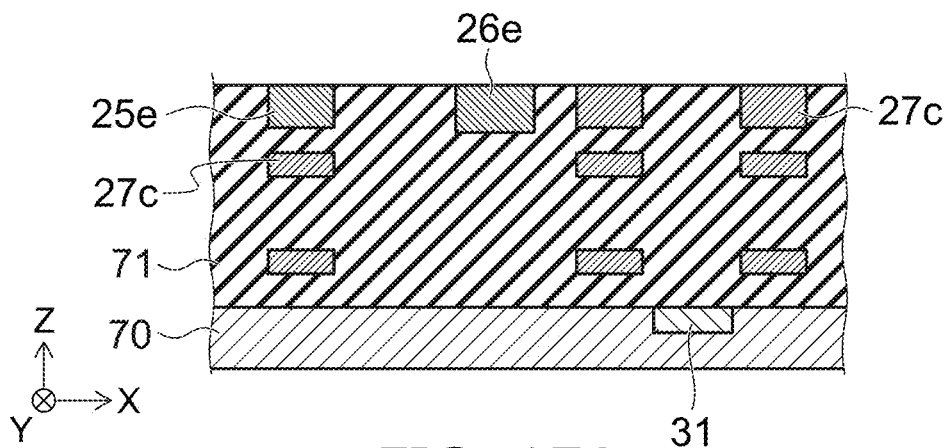
FIG. 17A to FIG. 17C are schematic cross-sectional views illustrating a method for manufacturing the sensor according to the second embodiment.

As shown in FIG. 17A, the optical sensor 31 (e.g., a photodiode) is formed in the base body 70 (e.g., a silicon substrate with impurity). The interconnects 27c and a portion of the insulating layer 71 (e.g., $SiO_2$) are formed. The first electrode 25e and the second electrode 26e are formed. The interconnects 27c and the electrodes may include, for example, at least one of copper or aluminum. Other materials may be included in these components. The upper surface of the insulating layer 71 may recede with respect to the upper surfaces of a portion of the interconnects 27c, the second electrode 26e, and the first electrode 25e.

Figure 17B:
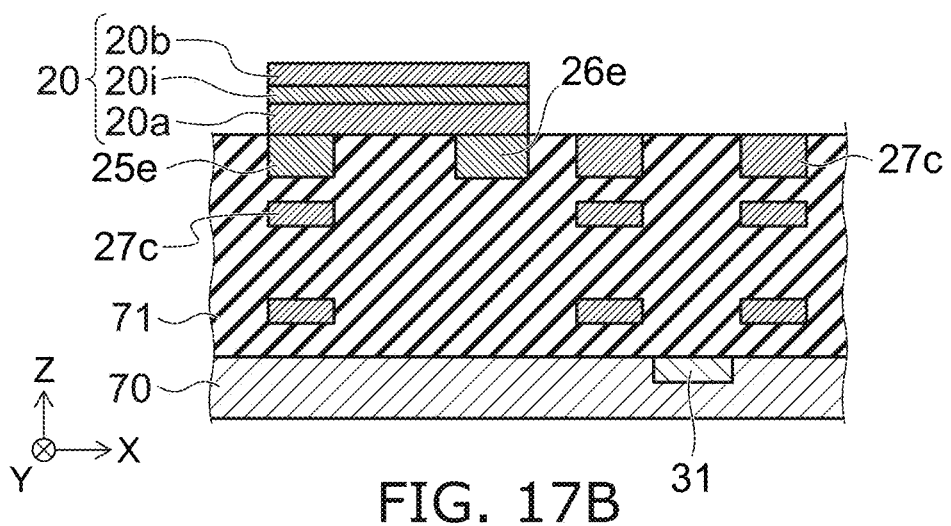

As shown in FIG. 17B, a film that is used to form the first magnetic layer 20a, a film that is used to form the intermediate layer 20i, and a film that is used to form the second magnetic layer 20b are formed; and a stacked body that includes the first magnetic layer 20a, the intermediate layer 20i, and the second magnetic layer 20b is formed by patterning these films. For example, the patterning includes forming a resist mask and etching via the resist mask.

Figure 17C:
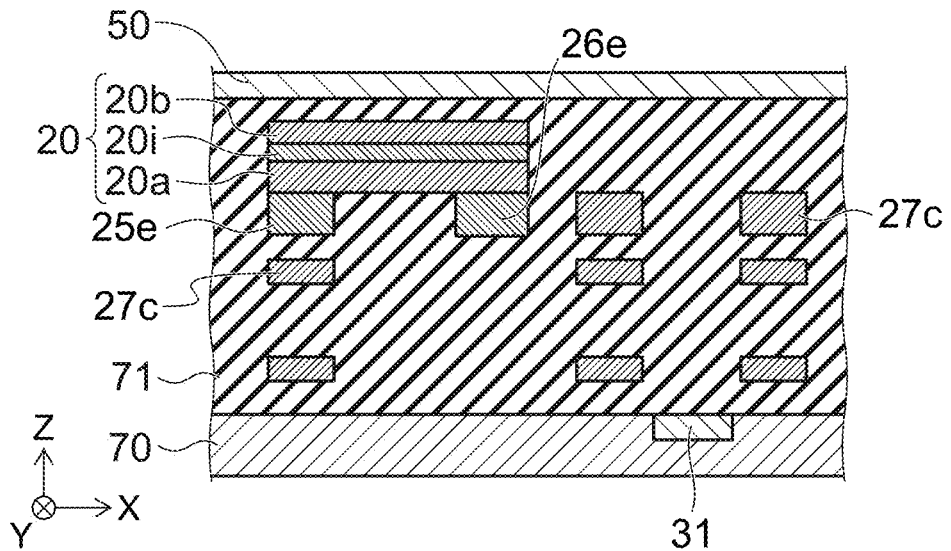

As shown in FIG. 17C, a $SiO_2$ film (a portion of the insulating layer 71) is formed; and the front surface is planarized by chemical mechanical polishing (CMP). Subsequently, for example, the nonmagnetic layer 50 (e.g., a SiN film) is formed by CVD.

Figure 18A:
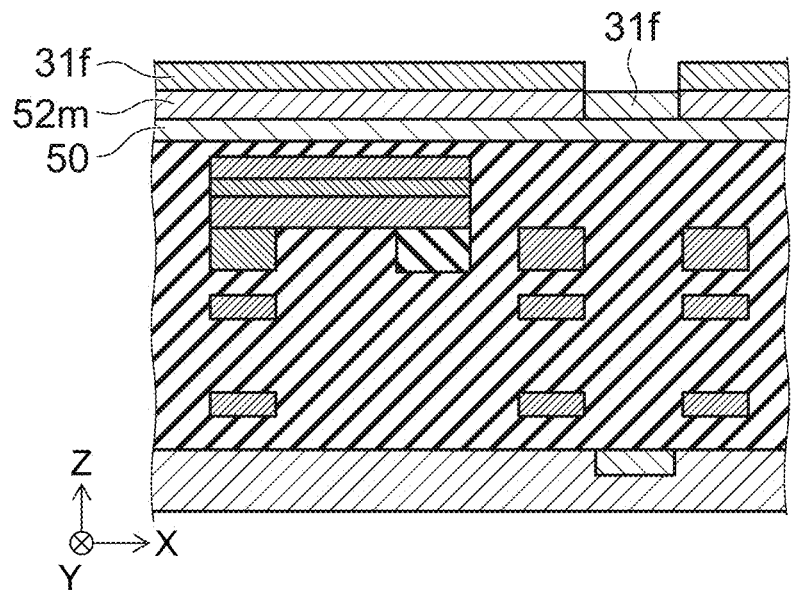
FIG. 18A and FIG. 18B are schematic cross-sectional views illustrating a method for manufacturing the sensor according to the second embodiment.

As shown in FIG. 18A, a $SiO_2$ film that is used to form the partition 52 is formed on the nonmagnetic layer 50; a resist mask 52m is formed; and a portion of the $SiO_2$ film is removed by etching. Thereby, a portion of the nonmagnetic layer 50 is exposed.

Figure 18B:
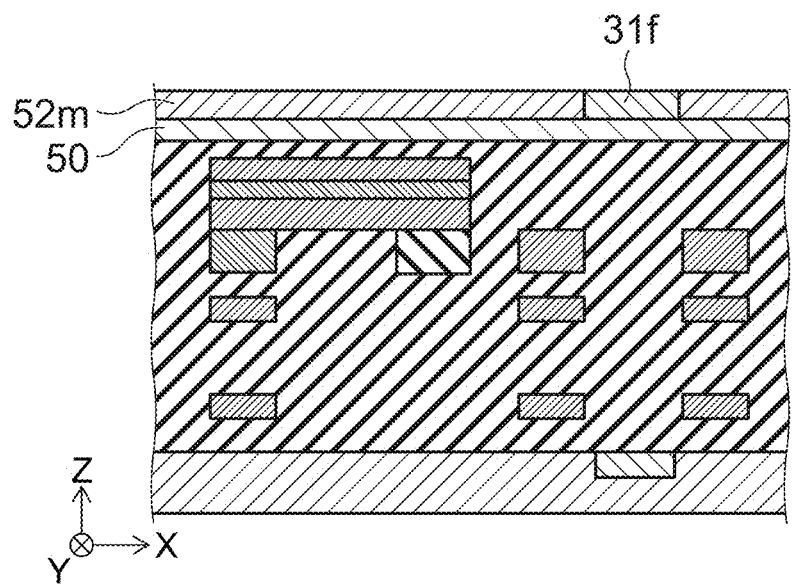

As shown in FIG. 18B, a film (e.g., a multilayer film) that is used to form the optical filter 31f is formed on the exposed portion of the nonmagnetic layer 50 and on the resist mask 52m. For example, the multilayer film is formed by sputtering, etc. Subsequently, the resist mask 52m is removed; and the optical filter 31f is formed by lift-off.

Thereby, the sensor 123 is made. The sensors 110 and 120 to 122 recited above are manufactured by appropriately modifying the manufacturing method recited above. The sensors, etc., described below also are manufactured by appropriately modifying the manufacturing method recited above.

Figure 19A:
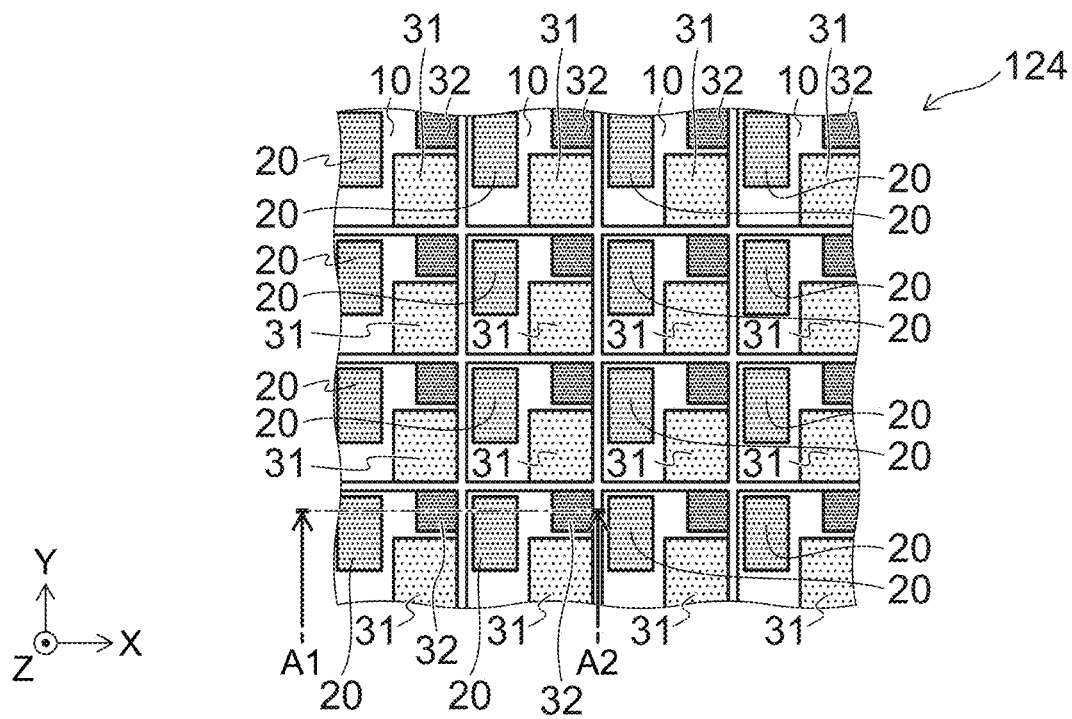
FIG. 19A and FIG. 19B are schematic views illustrating another sensor according to the second embodiment.
Figure 19B:
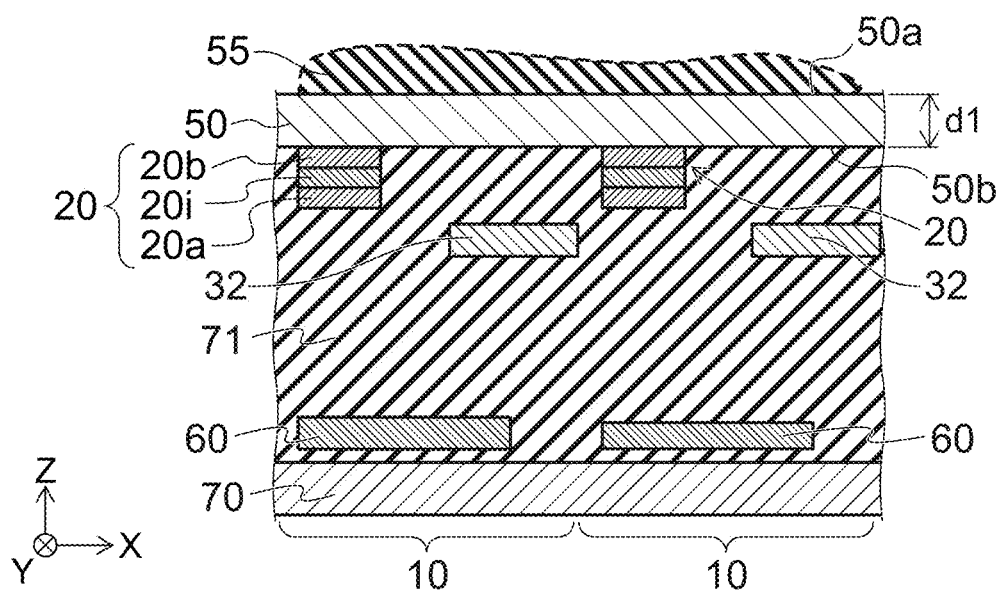

FIG. 19A and FIG. 19B are schematic views illustrating another sensor according to the second embodiment.

FIG. 19A is a plan view. FIG. 19B is a cross-sectional view.

As shown in FIG. 19A and FIG. 19B, compared to the sensor 120, the sensor 124 according to the embodiment further includes multiple other sensors 32. The multiple other sensors 32 are arranged along the second surface 50b of the nonmagnetic layer 50.

The multiple other sensors 32 include, for example, at least one of a chemical sensor, a temperature sensor, or an electrical sensor. For example, the electrical sensor senses at least one of the current (movement of the electrical potential) in the specimen 55, the voltage (electrical potential) of the specimen 55, or the impedance of the specimen 55. Several examples of the other sensors will now be described.

Figure 20:
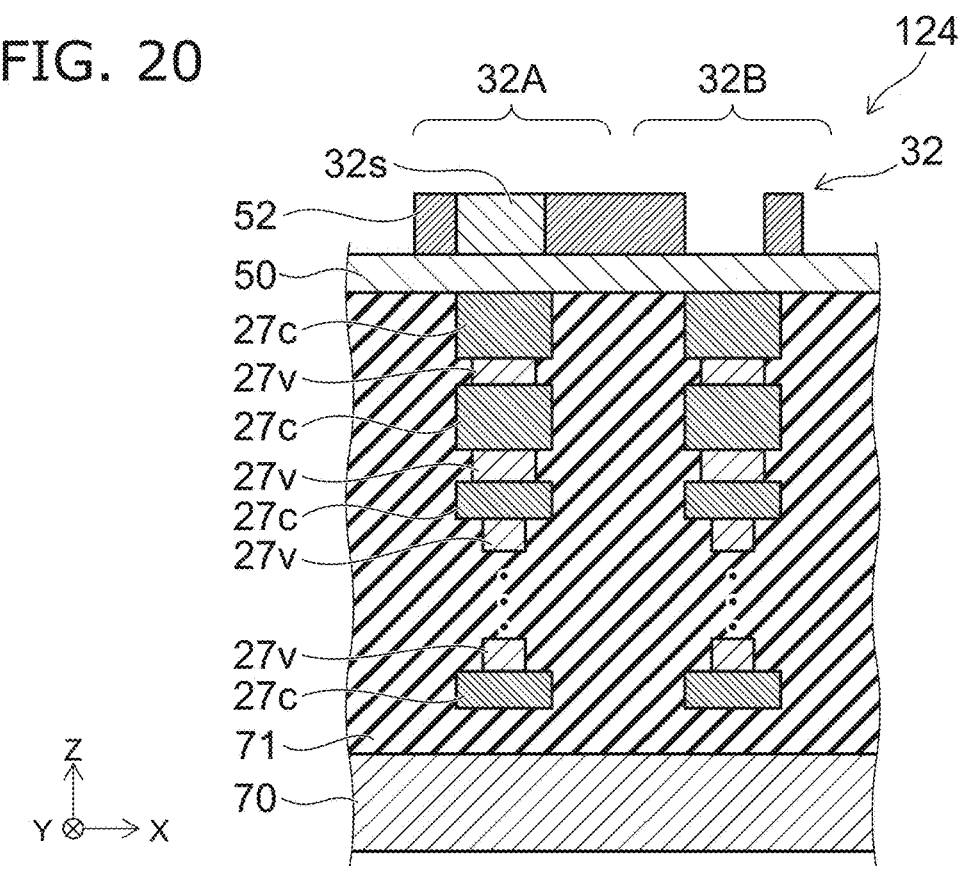
FIG. 20 is a schematic cross-sectional view illustrating a portion of the other sensor according to the second embodiment.

FIG. 20 is a schematic cross-sectional view illustrating a portion of the other sensor according to the second embodiment.

FIG. 20 shows an example of a chemical sensor. As shown in FIG. 20, the chemical sensor 32 includes, for example, an ion detecting element 32A and a hydrogen ion detecting element 32B. The nonmagnetic layer 50 is provided between the interconnects 27c and the ion detecting element 32A and between the interconnects 27c and the hydrogen ion detecting element 32B.

The ion detecting element 32A includes, for example, an ion-sensitive film 32s. The nonmagnetic layer 50 is provided between the interconnects 27c and the ion-sensitive film 32s. The ion-sensitive film 32s includes, for example, polyvinyl chloride (PVC). The PVC is, for example, a base material. The ion-sensitive film 32s further includes an ionophore. For example, the ionophore selectively bonds with ions of a different type. The ionophore includes, for example, valinomycin, etc. The ion-sensitive film 32s may further include at least one of a plasticizer or an excluder. The ionophore that bonds with the ions includes, for example, at least one of $Na^+$:bis(12-crown-4), $K^+$:bis(benzo-15-crown-5), valinomycin, $Ca^+$:K23E1, or $NH_4^+$:TD19C6. A transistor (not illustrated) may be connected to the ion detecting element 32A. The transistor may be provided in the base body 70. The transistor senses the change of the ion concentration of the ion-sensitive film 32s.

In the case where the ion detecting element 32A is provided, the nonmagnetic layer 50 may include at least one of silicon oxide, aluminum oxide, or tantalum oxide.

In the hydrogen ion detecting element 32B, the nonmagnetic layer 50 (the SiN film) functions as a hydrogen ion sensor film. The hydrogen ions are sensed by having silanol groups occurring at the front surface of the SiN film as functional groups. A transistor (not illustrated) may be connected to the hydrogen ion detecting element 32B. The transistor may be provided in the base body 70. The transistor senses the change of the hydrogen ion concentration.

Figure 21:
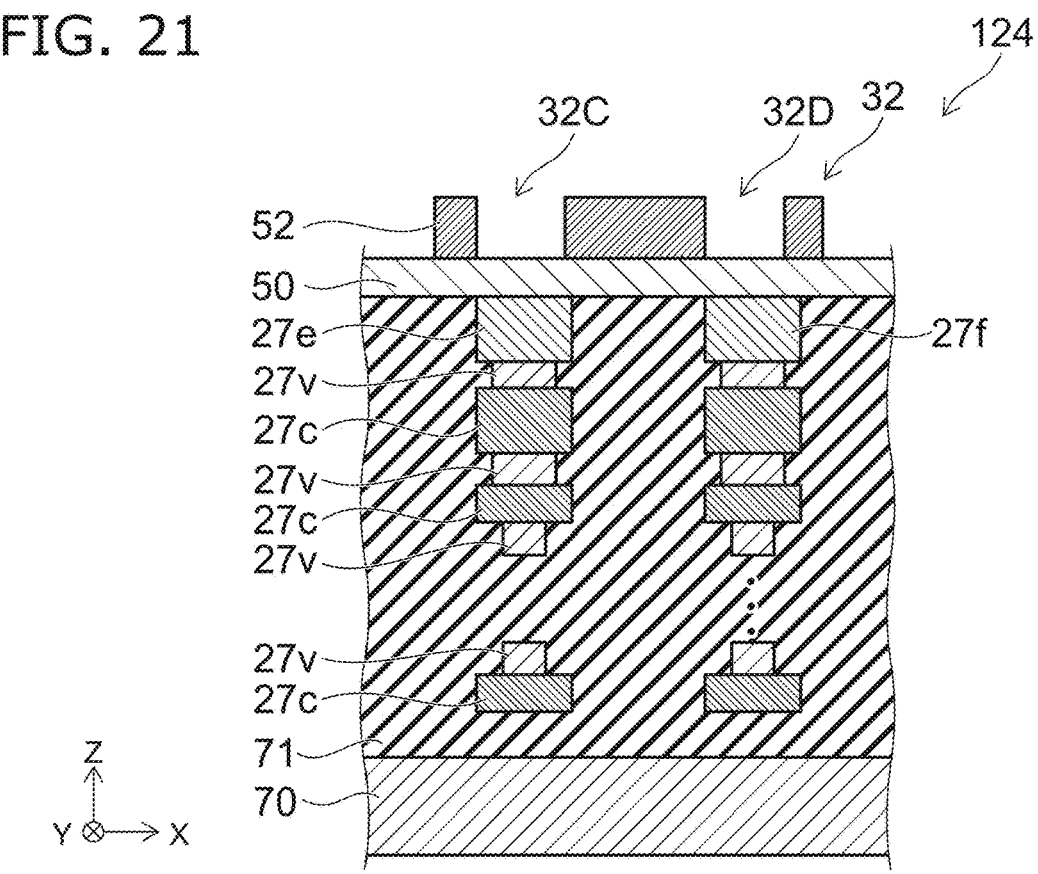
FIG. 21 is a schematic cross-sectional view illustrating a portion of another sensor according to the second embodiment.

FIG. 21 is a schematic cross-sectional view illustrating a portion of another sensor according to the second embodiment.

FIG. 21 shows an example of an electrical sensor and a temperature sensor. As shown in FIG. 21, an electrode 27e is provided between the nonmagnetic layer 50 (e.g., the SiN film) and the interconnects 27c. The nonmagnetic layer 50 is disposed between the specimen 55 and the electrode 27e. Capacitive coupling via the nonmagnetic layer 50 is formed between the specimen 55 and the electrode 27e. The change of the electrical potential in the specimen 55 is sensed by sensing the change in the capacitance. The electrode 27e may include, for example, at least one of Ni, Pt, Au, or Ti.

For example, the temperature dependence of the threshold voltage of a field effect transistor (FET) is utilized in a temperature sensor 32D. The temperature sensor 32D may include, for example, a transistor circuit including multiple field effect transistors. For example, the circuit includes an electrode 27f, a first FET that is connected to the electrode 27f, a second FET that has a diode connection in series with the first FET, and a third FET that is connected in parallel with the series circuit of the first and second FETs. The temperature sensor may not occupy a region of the front surface of the sensor 124. Such a configuration that utilizes multiple FETs may be provided as an independent temperature sensor element.

Third Embodiment

Figure 22:
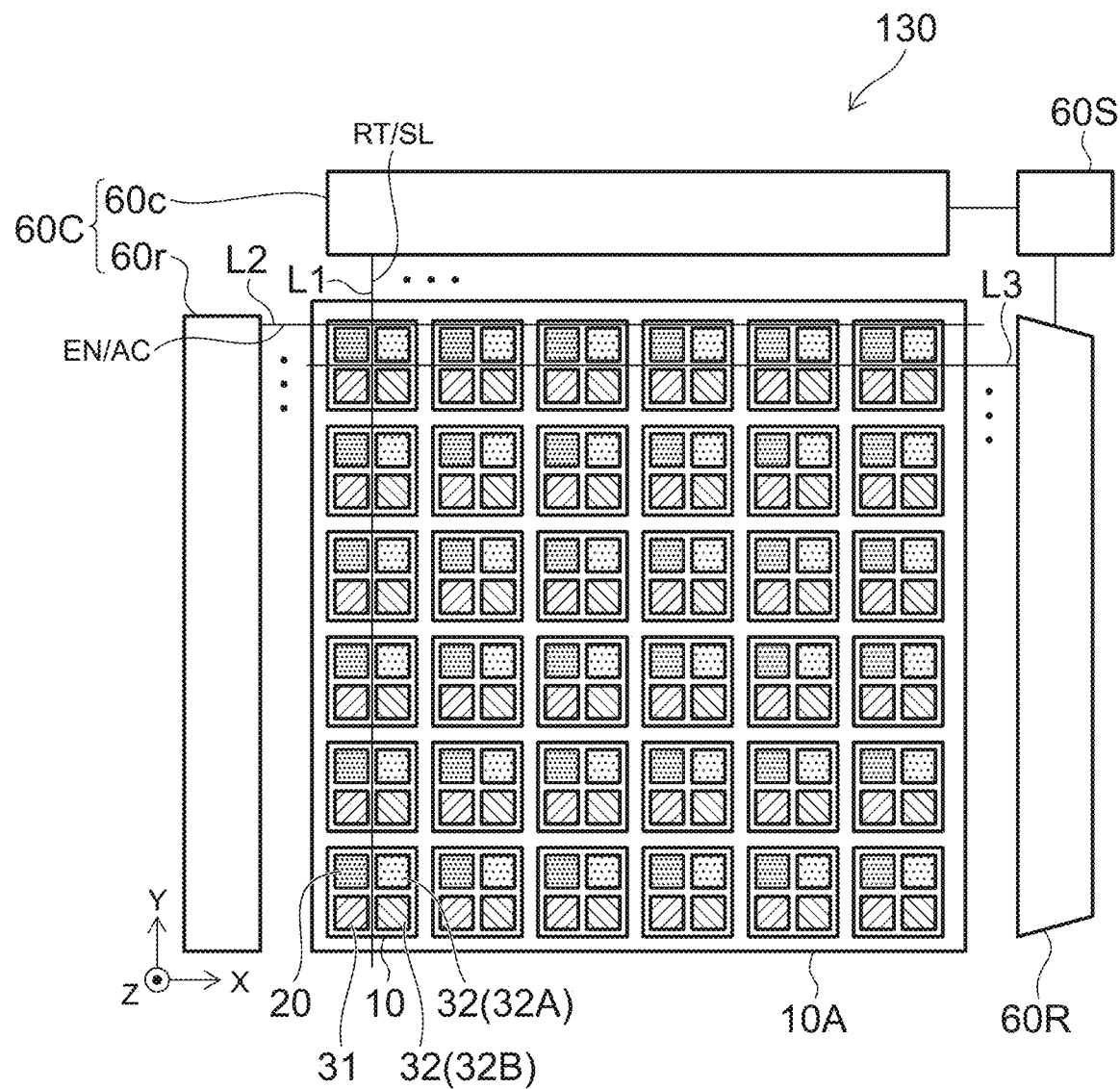
FIG. 22 is a schematic plan view illustrating a sensor according to a third embodiment.

FIG. 22 is a schematic plan view illustrating a sensor according to a third embodiment.

As shown in FIG. 22, the sensor according to the third embodiment includes the multiple magnetic field sensors 20 and the nonmagnetic layer 50 (not illustrated in FIG. 22) described in reference to the first and second embodiments. The multiple sensing components 10 are provided in the example. One of the multiple sensing components 10 includes at least one of the multiple magnetic field sensors 20, at least one of the multiple optical sensors, and at least one of the multiple other sensors 32. In the example, the ion detecting element 32A and the hydrogen ion detecting element 32B are provided as the other sensor 32. The multiple sensing components 10 are arranged in the X-axis direction and the Y-axis direction. The multiple sensing components 10 are included in a sensor array 10A (a pixel array).

The sensor 130 further includes a selection circuit 60C, a read circuit 60R, and a current supply circuit 60S. The selection circuit 60C selects the multiple magnetic field sensors 20. In other words, the selection circuit 60C selects the multiple sensing components 10. The read circuit 60R reads the states of the multiple magnetic field sensors 20. The current supply circuit 60S supplies an electric current to the multiple magnetic field sensors 20.

The selection circuit 60C includes a column controller 60c and a row controller 60r. Multiple first interconnects L1 are connected to the column controller 60c. For example, the multiple first interconnects L1 extend in the Y-axis direction and are arranged in the X-axis direction. Multiple second interconnects L2 are connected to the row controller 60r. For example, the multiple second interconnects L2 extend in the X-axis direction and are arranged in the Y-axis direction. Multiple third interconnects L3 are connected to the read circuit 60R. For example, the multiple third interconnects L3 extend in the X-axis direction and are arranged in the Y-axis direction.

For example, the column controller 60c and the row controller 60r control the data sensing operations of the multiple sensing components 10. For example, the column controller 60c and the row controller 60r control the read order of the data from, for example, the multiple magnetic field sensors 20.

For example, the row controller 60r generates an enable signal EN and an activation signal AC. These signals are provided to the multiple second interconnects L2. For example, the element that is selected is set to the operating state by the enable signal EN. For example, the electrical power for the element selected to function is supplied by the activation signal AC.

The column controller 60c generates a reset signal RT and a transfer signal SL. These signals are provided to the multiple first interconnects L1. For example, the input voltage of the amplifier amplifying the sense signal from the sensor is reset by the reset signal RT. For example, an output signal Vo of the amplifier is transferred to the read circuit 60R by the transfer signal SL.

The read circuit 60R includes, for example, a multiplexer.

For example, the sensor circuit portion 60 illustrated in FIG. 1B may include at least a portion of the read circuit 60R recited above. The sensor circuit portion 60 may include at least a portion of the selection circuit 60C recited above. The sensor circuit portion 60 may include at least a portion of the current supply circuit 60S recited above.

Figure 23:
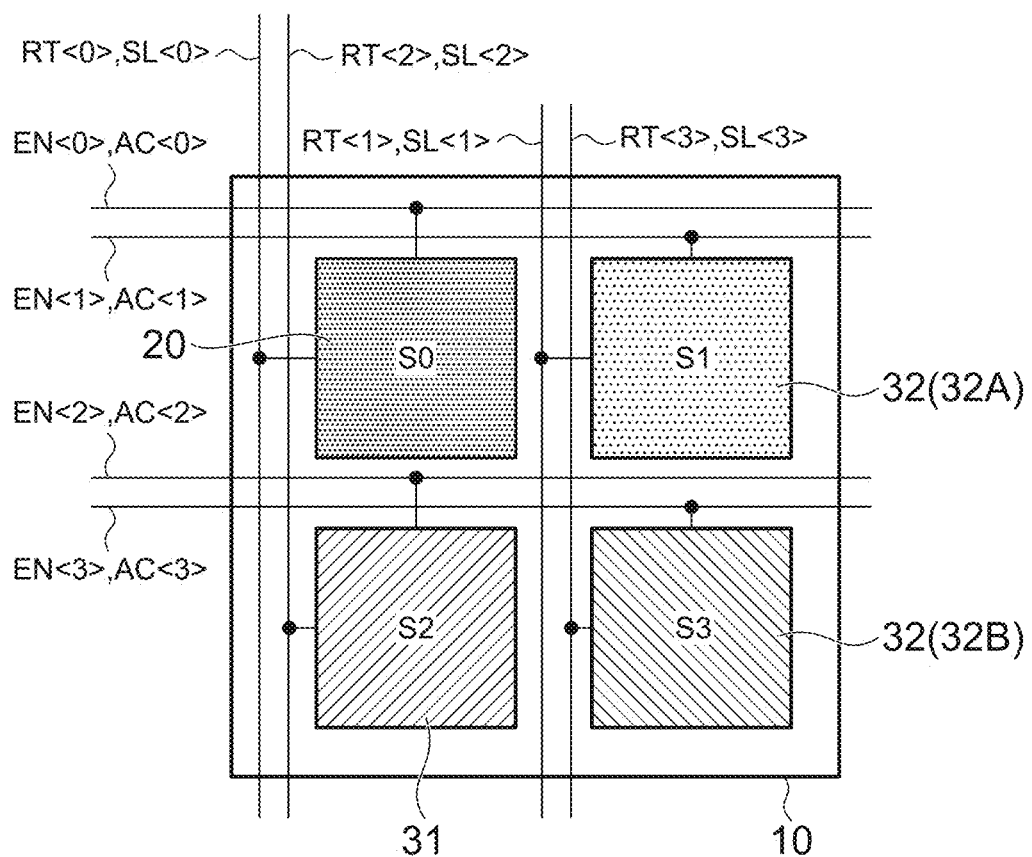
FIG. 23 is a schematic plan view illustrating a portion of the sensor according to the third embodiment.

FIG. 23 is a schematic plan view illustrating a portion of the sensor according to the third embodiment.

FIG. 23 schematically shows the circuit configuration of the periphery of one of the multiple sensing components 10.

In the example, four types of sensor elements (sensor elements S0, S1, S2, and S3) are provided in one sensing component 10.

The enable signal EN<0:3> and the activation signal AC<0:3> are provided to one sensing component 10. For example, the enable signal EN<0> and the activation signal AC<0> are provided to the sensor element S0. For example, the enable signal EN<1> and the activation signal AC<1> are provided to the sensor element S1. The enable signal EN<2> and the activation signal AC<2> are provided to the sensor element S2. The enable signal EN<3> and the activation signal AC<3> are provided to the sensor element S3.

The reset signal RT<0:3> and the transfer signal SL<0:3> are provided to one sensing component 10. The reset signal RT<0> and the transfer signal SL<0> are provided to the sensor element S0. The reset signal RT<1> and the transfer signal SL<1> are provided to the sensor element S1. The reset signal RT<2> and the transfer signal SL<2> are provided to the sensor element S2. The reset signal RT<3> and the transfer signal SL<3> are provided to the sensor element S3.

Figure 24:
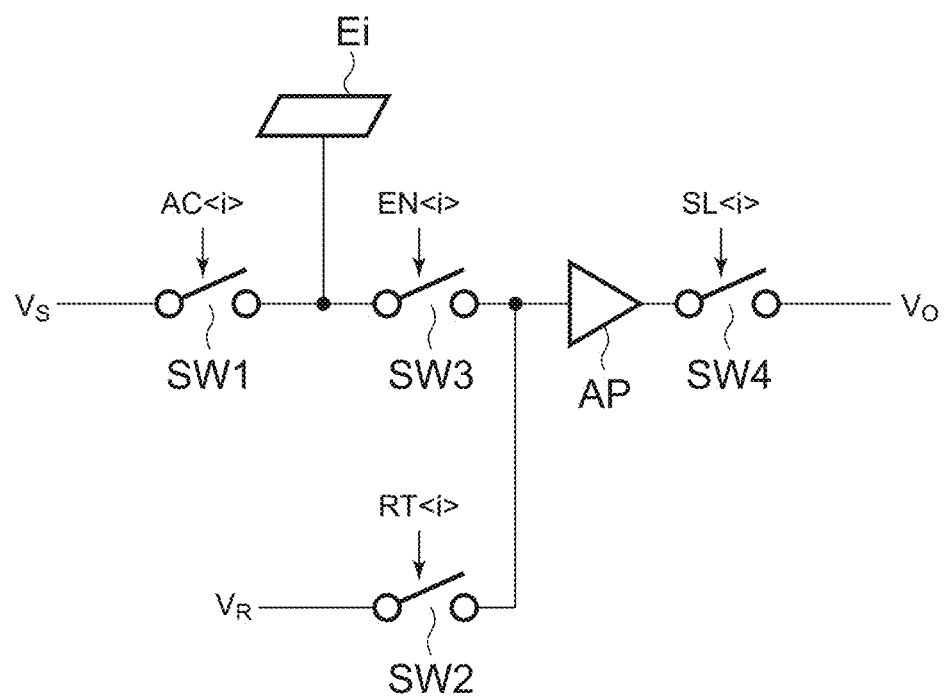
FIG. 24 is a schematic view illustrating a portion of the sensor according to the third embodiment.

FIG. 24 is a schematic view illustrating a portion of the sensor according to the third embodiment.

FIG. 24 shows an example of a circuit of one of the sensor element S0, S1, S2, or S4 shown in FIG. 23. The circuit includes a switch element SW1, a switch element SW2, a switch element SW3, and a switch element SW4. Hereinbelow, "i" is an integer of 0 to 3. The switch element SW1 applies a power supply voltage VS to an electrode Ei connected to the sensor due to the activation signal AC<i>. The switch element SW2 resets the input of an amplifier AP to a reset voltage VR based on the reset signal RT<i>. The switch element SW3 transfers the sense signal from the electrode Ei to the amplifier AP based on the enable signal EN<i>. The switch element SW4 enables the output signal Vo of the amplifier AP based on the transfer signal SL<i>.

At least one of the switch element SW1, SW2, SW3, or SW4 includes, for example, at least one of a P-channel MOS transistor, an N-channel MOS transistor, or a CMOS switch including these transistors. The amplifier AP includes at least one of a source-grounded amplifier, a drain-grounded amplifier, or a differential amplifier.

The sensor 130 may further include an A/D converter circuit. The sensor 130 may include a signal processing circuit that processes the signal from the sensor element according to a preset method. For example, the signal processing circuit implements at least one of time integration, averaging, differencing, autozeroing, chopping, correlated double sampling, or correlated multiple sampling. The sensor 130 may further include a communication circuit that transmits the obtained result to the outside. The sensor 130 may further include a memory circuit that stores at least one of the measurement conditions, the measurement method, the correspondence with the samples, or the obtained results.

Fourth Embodiment

Figure 25:
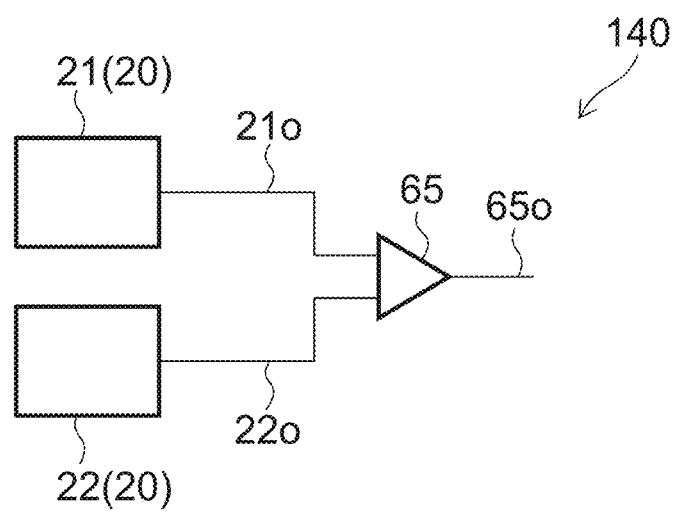
FIG. 25 is a schematic view illustrating a sensor according to a fourth embodiment.

FIG. 25 is a schematic view illustrating a sensor according to a fourth embodiment.

As shown in FIG. 25, the sensor 140 according to the embodiment includes a differentiating circuit 65 in addition to the multiple magnetic field sensors 20. The differentiating circuit 65 outputs the value (an output 65o) of the differentiating of an output 21o of one of the multiple magnetic field sensors 20 (e.g., the first magnetic field sensor 21) and an output 22o of one other of the multiple magnetic field sensors 20 (e.g., the second magnetic field sensor 22).

For example, the position of the first magnetic field sensor 21 and the second magnetic field sensor 22 are arbitrary. For example, the first magnetic field sensor 21 and the second magnetic field sensor 22 may be arranged in the X-axis direction. For example, the first magnetic field sensor 21 and the second magnetic field sensor 22 may be arranged in the Y-axis direction. For example, the first magnetic field sensor 21 and the second magnetic field sensor 22 may be arranged in a direction tilted with respect to the X-axis direction.

According to the sensor 140, the output images of the multiple magnetic field sensors 20 can be compared. For example, the position of the source of the magnetic field can be estimated. For example, the source of the magnetic field is at a designated position inside the specimen 55.

For example, as described in reference to FIG. 5A, FIG. 5B, FIG. 6A, and FIG. 6B, magnetic field Bx generated from the specimen 55 decreases abruptly outside of an area with some distance.

When the number of the peaks of the magnetic field Bx is 1, differentiating the outputs of the multiple magnetic field sensors 20 as in the sensor 140 gives multiple (two) peaks. The two peaks obtained from the differentiation correspond to differentials of one peak. The positions of the two peaks are at some distance from the center of the one peak (magnetic field source). Thereby, even in the case where the pitch of the multiple magnetic field sensors 20 is large, high-precision sensing can be possible by sensing the differentiated peaks.

Figure 26A:
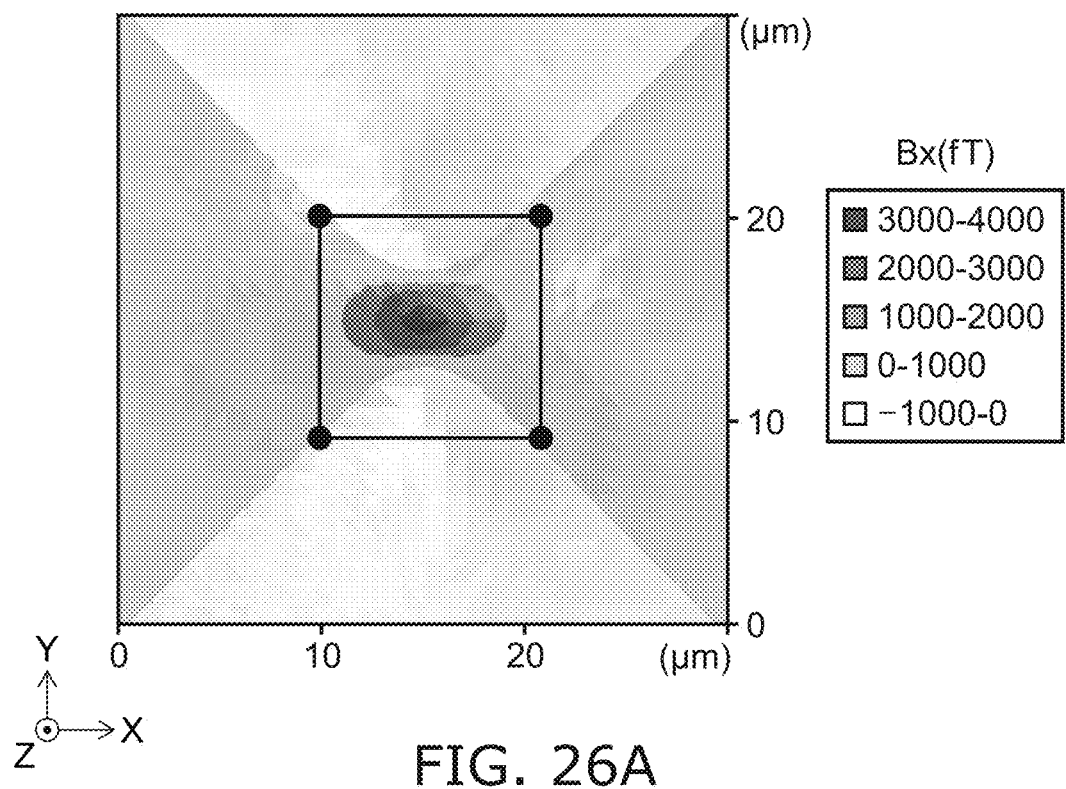
FIG. 26A and FIG. 26B are schematic views illustrating characteristics of the sensor according to the fourth embodiment.
Figure 26B:
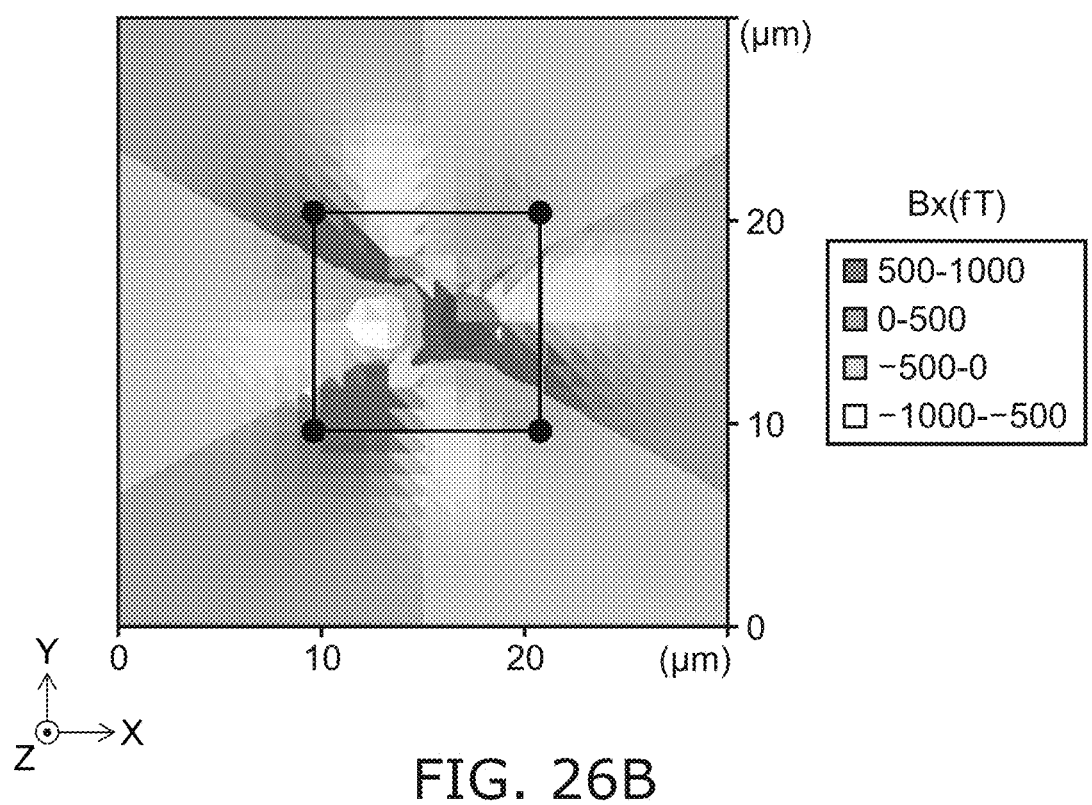

FIG. 26A and FIG. 26B are schematic views illustrating characteristics of the sensor according to the fourth embodiment.

FIG. 26A illustrates the magnetic field Bx sensed by the multiple magnetic field sensors 20. In the example, the lengths in the X-axis direction and the lengths in the Y-axis direction of the multiple magnetic field sensors 20 are 3 μm each. The distance d1 (referring to FIG. 1B) is 1 μm. The distribution of the magnetic field Bx is plotted with a spatial resolution of 1 μm. FIG. 26B is the result of differencing the magnetic field Bx shown in FIG. 26A along the X-axis direction. The black round symbols inside these figures show the positions of four magnetic field sensors 20 when the multiple magnetic field sensors 20 are arranged at a pitch of 10 μm.

As shown in FIG. 26A, the distribution of the magnetic field Bx has one peak. In such a case, the magnetic field Bx is about 30 fT at the four positions.

Conversely, as shown in FIG. 26B, the distribution of the magnetic field Bx has two peaks by differencing the outputs of the multiple magnetic field sensors 20. In this case, the magnetic field Bx at the four positions is, for example, −70 fT. That is, the sensing strength increases. This differencing procedure decreases the probability of the case when the four magnetic field sensors 20 are placed at the worst position, where detected Bx becomes extremely low.

Thus, the sensing efficiency is increased by differencing the outputs of the multiple magnetic field sensors 20. Further, by differencing, the background noise due to geomagnetism, etc., can be suppressed. Thereby, the sensing efficiency increases further.

For example, the differencing recited above may be performed at a high frequency. The frequency of the high frequency is, for example, not less than 0.8 kHz and not more than 1.5 kHz. For example, the background magnetic field noise that is caused by an alternating current power supply is suppressed. For example, multiple magnetic field sensors 20 are switched with a frequency of about 1 kHz and differencing procedure is performed successively with the time rate of 1 kHz.

To provide a society in which one can be healthier and live comfortably, research for clarifying the cause of illnesses, the pathogenesis mechanisms, etc., is important. Research relating to preventive methods, therapeutic methods, etc. are also important. Methods to collect information relating to illnesses and information of the causes of illnesses in humans (e.g., congenital factors, lifestyle factors, acquired factors, etc.) is investigated to reduce the risk of illnesses. Analyzing method of such information has also been studied.

For example, it is desirable to develop biosensors that efficiently collect more detailed information. It is desirable to provide a biosensor in which information of multiple characteristics (multi-item) can be obtained.

In the embodiment, for example, a magnetic field sensor is used. Further, an optical sensor may be used. The temporal change of the activities in the specimen 55 can be measured in real time. For example, the activity (the current pulse signal flowing through a nerve, etc.) of the specimen 55 can be measured in real time as a magnetic field. By acquiring the magnetic field data as a pixel, information in which real image of the specimen and its activity condition are unified can be measured in real time.

By mounting other multiple sensors in the same pixel (basic block), multiple vital signs of the specimens 55 can be sensed simultaneously. Moreover, the evaluation can be performed more rapidly. The comprehensive analysis from the results obtained for multiple vital signs is possible. More accurate analysis is possible. Excellent analysis is possible. According to the biosensor of the embodiment, for example, information of multiple characteristics (multi-item) is obtained with higher reliability.

The embodiments may include the following configurations.
(Configuration 1)
A sensor, comprising:
a nonmagnetic layer having a first surface and a second surface; and
a plurality of magnetic field sensors arranged along the second surface,
the second surface being between the first surface and the plurality of magnetic field sensors, each of the plurality of magnetic field sensors including
a first magnetic layer,
a second magnetic layer provided between the first magnetic layer and the nonmagnetic layer, and
an intermediate layer provided between the first magnetic layer and the second magnetic layer, the intermediate layer being nonmagnetic,
a distance between the first surface and the second magnetic layer being not more than a pitch of the plurality of magnetic field sensors.
(Configuration 2)
The sensor according to configuration 1, wherein the distance is 10 micrometers or less.
(Configuration 3)
The sensor according to configuration 1 or 2, wherein a specimen is arrangeable at the first surface.
(Configuration 4)
The sensor according to one of configurations 1 to 3, wherein
at least a portion of the plurality of magnetic field sensors is arranged along a first arrangement direction aligned with the second surface, and at least a portion of the plurality of magnetic field sensors is arranged along a second arrangement direction, the second arrangement direction crossing the first arrangement direction and being aligned with the second surface.

(Configuration 5)

The sensor according to one of configurations 1 to 3, wherein at least a portion of the plurality of magnetic field sensors is arranged at a first pitch along a first arrangement direction, the first arrangement direction being aligned with the second surface, and the first pitch is not less than 2 times and not more than 1000 times of the distance.

(Configuration 6)

The sensor according to configuration 5, wherein at least a portion of the plurality of magnetic field sensors is arranged at a second pitch along a second arrangement direction, the second arrangement direction crossing the first arrangement direction and being aligned with the second surface, and the second pitch is not less than 2 times and not more than 1000 times of the distance.

(Configuration 7)

The sensor according to one of configurations 1 to 3, wherein at least a portion of the plurality of magnetic field sensors is arranged at a first pitch along a first arrangement direction, the first arrangement direction being aligned with the second surface, and the first pitch is 14 μm or less.

(Configuration 8)

The sensor according to configuration 7, wherein at least a portion of the plurality of magnetic field sensors is arranged at a second pitch along a second arrangement direction, the second arrangement direction crossing the first arrangement direction and being aligned with the second surface, and the second pitch is 14 μm or less.

(Configuration 9)

The sensor according to one of configurations 1 to 8, wherein the plurality of magnetic field sensors includes a first magnetic field sensor and a second magnetic field sensor, a length of the first magnetic field sensor along a first extension direction aligned with the second surface is longer than a length of the first magnetic field sensor along a direction perpendicular to the first extension direction and aligned with the second surface, and a length of the second magnetic field sensor along a second extension direction is longer than a length of the second magnetic field sensor along a direction perpendicular to the second extension direction and aligned with the second surface, the second extension direction crossing the first extension direction and being aligned with the second surface.

(Configuration 10)

The sensor according to configuration 9, wherein the first magnetic field sensor is multiply provided, the second magnetic field sensor is multiply provided, one of the plurality of second magnetic field sensors is disposed between two of the plurality of first magnetic field sensors, and one of the plurality of first magnetic field sensors is disposed between two of the plurality of second magnetic field sensors.

(Configuration 11)

The sensor according to one of configurations 3 to 10, wherein at least one of the plurality of magnetic field sensors outputs a sense signal corresponding to a pulse signal generated at the specimen.

(Configuration 12)

The sensor according to one of configurations 1 to 11, wherein the specimen includes a living body.

(Configuration 13)

The sensor according to one of configurations 1 to 12, further comprising a plurality of optical sensors arranged along the second surface, at least one of the plurality of magnetic field sensors and at least one of the plurality of optical sensors being included in one of a plurality of sensing components.

(Configuration 14)

The sensor according to one of configurations 1 to 13, wherein a distance between the first surface and the at least one of the plurality of magnetic field sensors is shorter than a distance between the first surface and the at least one of the plurality of optical sensors.

(Configuration 15)

The sensor according to one of configurations 1 to 14, further comprising a plurality of other sensors arranged along the second surface, at least one of the plurality of magnetic field sensors and at least one of the plurality of other sensors being included in one of a plurality of sensing components, one of the plurality of other sensors including at least one of a chemical sensor, a temperature sensor, or an electrical sensor.

(Configuration 16)

The sensor according to one of configurations 1 to 15, further comprising a sensor circuit portion connected to at least one of the plurality of magnetic field sensors, at least a portion of the plurality of magnetic field sensors being disposed between the nonmagnetic layer and at least a portion of the sensor circuit portion in a direction from the second surface toward the first surface.

(Configuration 17)

The sensor according to configuration 16, wherein the sensor circuit portion includes at least a portion of a read circuit reading a state of the plurality of magnetic field sensors.

(Configuration 18)

The sensor according to one of configurations 1 to 17, further comprising:

a selection circuit selecting the plurality of magnetic field sensors; and a read circuit reading a state of the plurality of magnetic field sensors.

(Configuration 19)

The sensor according to configuration 18, further comprising a current supply circuit supplying a current to the plurality of magnetic field sensors.

(Configuration 20)

The sensor according to one of configurations 1 to 19, further comprising a difference circuit outputting a value made by differencing an output of one of the plurality of magnetic field sensors and an output of one other of the plurality of magnetic field sensors.

According to the embodiments, a sensor can be provided in which it is possible to sense the state of the specimen more accurately.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as magnetic sensors, magnetic layers, intermediate layers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
   a nonmagnetic layer having a first surface configured to accept placement of a biological specimen and a second surface; and
   a plurality of magnetic field sensors arranged along the second surface,
   the second surface being between the first surface and the magnetic field sensors, each of the magnetic field sensors including
   a first magnetic layer,
   a second magnetic layer provided between the first magnetic layer and the nonmagnetic layer, and
   an intermediate layer provided between the first magnetic layer and the second magnetic layer, the intermediate layer being nonmagnetic,
   a distance between the first surface and the second magnetic layer being not more than a pitch of the magnetic field sensors,
   wherein at least one of the magnetic field sensors is configured to output a sense signal corresponding to a pulse signal generated in the specimen and to detect a temporal change in a spatial distribution of the sense signal,
   the magnetic field sensors include a first magnetic field sensor and a second magnetic field sensor,
   a length of the first magnetic field sensor along a first extension direction aligned with the second surface is longer than a length of the first magnetic field sensor along a direction perpendicular to the first extension direction and aligned with the second surface,
   a length of the second magnetic field sensor along a second extension direction is longer than a length of the second magnetic field sensor along a direction perpendicular to the second extension direction and aligned with the second surface, the second extension direction crossing the first extension direction and being aligned with the second surface,
   the first magnetic field sensor is multiply provided,
   the second magnetic field sensor is multiply provided,
   one of the second magnetic field sensors is disposed between two of the first magnetic field sensors, and
   one of the first magnetic field sensors is disposed between two of the second magnetic field sensors.

2. The sensor according to claim 1, wherein the distance is 10 micrometers or less.

3. The sensor according to claim 1, wherein
   at least a portion of the magnetic field sensors is arranged along a first arrangement direction aligned with the second surface, and
   at least a portion of the magnetic field sensors is arranged along a second arrangement direction, the second arrangement direction crossing the first arrangement direction and being aligned with the second surface.

4. The sensor according to claim 1, wherein
   at least a portion of the magnetic field sensors is arranged at a first pitch along a first arrangement direction, the first arrangement direction being aligned with the second surface, and
   the first pitch is not less than 2 times and not more than 1000 times of the distance.

5. The sensor according to claim 4, wherein
   at least a portion of the magnetic field sensors is arranged at a second pitch along a second arrangement direction, the second arrangement direction crossing the first arrangement direction and being aligned with the second surface, and
   the second pitch is not less than 2 times and not more than 1000 times of the distance.

6. The sensor according to claim 1, wherein
   at least a portion of the magnetic field sensors is arranged at a first pitch along a first arrangement direction, the first arrangement direction being aligned with the second surface, and
   the first pitch is 14 µm or less.

7. The sensor according to claim 6, wherein
   at least a portion of the magnetic field sensors is arranged at a second pitch along a second arrangement direction, the second arrangement direction crossing the first arrangement direction and being aligned with the second surface, and
   the second pitch is 14 µm or less.

8. The sensor according to claim 1, wherein the specimen includes a living body.

9. The sensor according to claim 1, further comprising a plurality of optical sensors arranged along the second surface,
   at least one of the magnetic field sensors and at least one of the optical sensors being included in one of a plurality of sensing components.

10. The sensor according to claim 9, wherein
    a distance between the first surface and the at least one of the magnetic field sensors is shorter than a distance between the first surface and the at least one of the optical sensors.

11. The sensor according to claim 1, further comprising a plurality of other sensors arranged along the second surface,
   at least one of the magnetic field sensors and at least one of the other sensors being included in one of a plurality of sensing components,
   one of the other sensors including at least one of a chemical sensor, a temperature sensor, or an electrical sensor.

12. The sensor according to claim 1, further comprising a sensor circuit portion connected to at least one of the magnetic field sensors,
   at least a portion of the magnetic field sensors being disposed between the nonmagnetic layer and at least a portion of the sensor circuit portion in a direction from the second surface toward the first surface.

13. The sensor according to claim 12, wherein the sensor circuit portion includes at least a portion of a read circuit reading a state of the magnetic field sensors.

14. The sensor according to claim 1, further comprising:
   a selection circuit selecting the magnetic field sensors; and
   a read circuit reading a state of the magnetic field sensors.

15. The sensor according to claim 14, further comprising a current supply circuit supplying a current to the magnetic field sensors.

16. The sensor according to claim 1, further comprising a difference circuit outputting a value made by differencing an output of one of the magnetic field sensors and an output of one other of the magnetic field sensors.

17. The sensor according to claim 1, wherein the first surface is configured to directly contact with the specimen.

18. A sensor, comprising:
   a nonmagnetic layer having a first surface and a second surface; and
   a plurality of magnetic field sensors arranged along the second surface,
   the second surface being between the first surface and the magnetic field sensors, each of the magnetic field sensors including
      a first magnetic layer,
      a second magnetic layer provided between the first magnetic layer and the nonmagnetic layer, and
      an intermediate layer provided between the first magnetic layer and the second magnetic layer, the intermediate layer being nonmagnetic,
   a distance between the first surface and the second magnetic layer being not more than a pitch of the magnetic field sensors
   wherein
      the magnetic field sensors include a first magnetic field sensor and a second magnetic field sensor,
      a length of the first magnetic field sensor along a first extension direction aligned with the second surface is longer than a length of the first magnetic field sensor along a direction perpendicular to the first extension direction and aligned with the second surface, and
      a length of the second magnetic field sensor along a second extension direction is longer than a length of the second magnetic field sensor along a direction perpendicular to the second extension direction and aligned with the second surface, the second extension direction crossing the first extension direction and being aligned with the second surface, and
      the first magnetic field sensor and the second magnetic field sensor each being multiply provided, such that one of the second magnetic field sensors is disposed between two of the first magnetic field sensors, and one of the first magnetic field sensors is disposed between two of the second magnetic field sensors.

* * * * *